United States Patent [19]
Suzuki et al.

[11] Patent Number: 5,891,671
[45] Date of Patent: Apr. 6, 1999

[54] METHOD FOR CLEAVING CHIMERIC PROTEIN USING PROCESSING ENZYME

[75] Inventors: Yuji Suzuki, Ashikaga; Koji Magota, Takatsuki; Toyofumi Masuda, Ibaraki, all of Japan

[73] Assignee: Suntory Limited, Osaka, Japan

[21] Appl. No.: 811,028

[22] Filed: Mar. 4, 1997

[30] Foreign Application Priority Data

Mar. 4, 1996 [JP] Japan .................................. 8-070906

[51] Int. Cl.⁶ ............................ C12P 21/06; C07K 14/00
[52] U.S. Cl. .................. 435/69.1; 435/252.3; 435/325; 530/350; 536/23.4
[58] Field of Search ........................ 530/350; 536/23.4; 435/69.1, 252.3, 325

[56] References Cited

FOREIGN PATENT DOCUMENTS 5-328 492  12/1993  Japan .

OTHER PUBLICATIONS

P.G. Seeboth et al., "In–Vitro Processing of Yeast α–Factor Leader Fusion Proteins Using a Soluble yscF (Kex2) Variant", *Applied Microbiology Biotechnology* (1991), vol. 35, pp. 771–776.
P.G. Seeboth et al., "In–Vitro Cleavage Of A Fusion Protein Bound To Cellulose Using the Soluble yscF$_s$ (Kex2) Variant", *Applied Microbiology Biotechnology* (1992), vol. 37, pp. 621–625.
Burgess et al. J. of Cell Biol. 11 : 2129–2138, 1990.
Lazar et al. Mol. Cell Biol. 8 : 1247–1252, 1988.
Tao et al. J. Immunol. 143(8) : 2595–2601, 1989.
Gillies et al. Human Antibodies & Hybridomas 1(1) : 47–54, 1990.
Wingender, E. et al. JBC. 264(8) : 4367–4373, 1989.
Friedman, TC. et al. Endocrinology 136(10):4462–4472, 1995.
Ledgerwood, EC et al. Biochem. J. 308 : 321–325, 1995.
Brennan, SO et al. FEBS letters. 347(1) : 80–84, 1994.
Diefenbach–Jagger, H. et al. Eur. J. Biochem, 229: 91–98, 1995.
Hendy, G.N. et al. JBC. 270(16): 9517–9525, 1995.
Jean et al. Biochem J. 292 : 891–900, 1993.
Koyama, N. et al. J. Biotechnol. 32(3) : 273–81, 1994.
Rouille, Y et al. JBC. 270(44) : 26488–26496, 1995.
Rothenberg, ME et al. JBC 270(17) : 10136–10146, 1995.
Drucker, DJ. Mol. Endocrinol 8(12) : 1646–55, 1994.

*Primary Examiner*—Lila Feisee
*Assistant Examiner*—Minh-Tam Davis
*Attorney, Agent, or Firm*—Burns, Doane, Swecker & Mathis, L.L.P.

[57] ABSTRACT

A chimeric protein is provided which comprises a target protein and has been designed so as to be easily cleaved by a processing enzyme, permitting a target protein to be efficiently recovered. The chimeric protein is represented by the following formula:

A-L-B wherein A represents a protective peptide;
B represents a target peptide; and
L represents a linker peptide having the sequence $X_1$-$X_2$-(Pro, Lys, or Arg)-Arg, wherein $X_1$ and $X_2$ represent any amino acid, in its C-terminal region and a domain rich in His in its N-terminal region.

17 Claims, 16 Drawing Sheets

Fig.1

```
                    U1                                    U2
5' AATTCATGAAATCTGTTAAAAAGCGTTCTGTTTCTGAAAT TCAGCTGATGCATAACCTGG
3'    GTACTTTAGACAATTTTTCGCAAGACAAAGACTTTAAGTCGACTAC GTATTGGACC
                                        L7            U3
   GCAAACACCTGAATAGCATGG AACGGCTCGAGTGCTGCGTAAGAAACTGCAGGACGTCC
   CGTTTGTGGACTTATCGTACC TTGCCGAGCT CACCGACGCATTCTTTGACGTCCTGCAGG
                    L6  U4                                  L5
                                                            U5
  AC AACTTCGTTCGCGCTGGGT GCACCGTGGCTCCACGTGATGC AGGATCCCAACGTCCGC
  TGTTGAAGCAAC GCGACCCACGTGGGCGACCGAGGTGCACTACGTCCTAGGGTT GCAGGCG
              L4
   GTAAGAAAGAAGATAACGTACT GGTTGAATCTCATGAGAAATCCCTGGGCGAAGCTGACA
   CATTCTTTCTTCTATTGCATGACCAACTTAGAG TACTCTTTAGGGACCCGCTTCGACTGT
  L3                      U6                              L2
                      U7
   AA GCCGATGTTAACGTGCTGACCAAAGCCGAAAAGCCAGTAAG         3'
      TTCGGCTACAATT GCACGACTGGTTTCGGCTTTTTCGGTCATTCAGCT 5'
                                L1
```

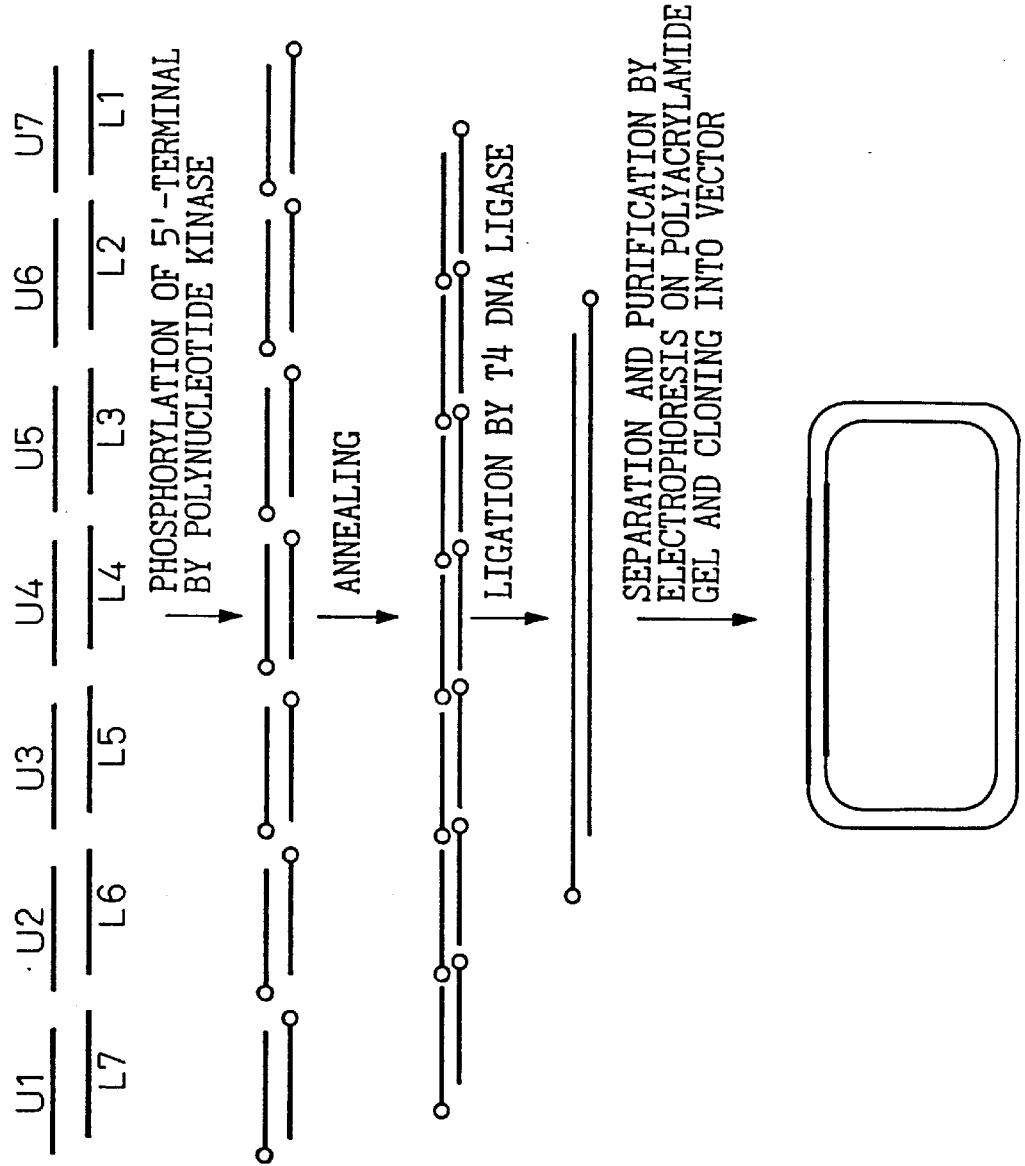

Fig. 4
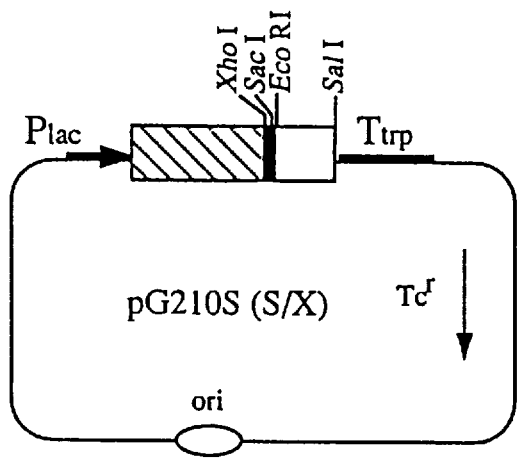
↓ Sac I/Xho I
↓ Exo III NUCLEASE
↓ MUNGBEAN NUCLEASE
↓ DNA POLYMERASE (KLENOW FRAGMENT)
↓ T4 DNA LIGASE
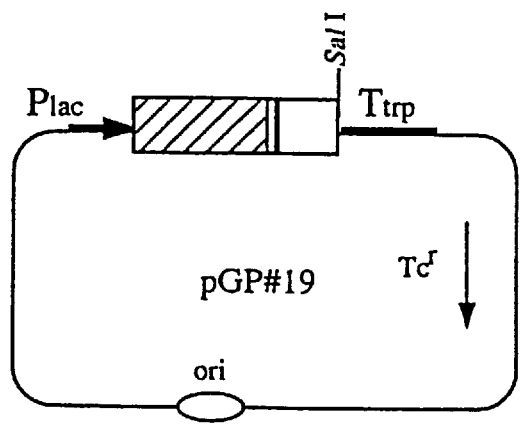

Fig. 8
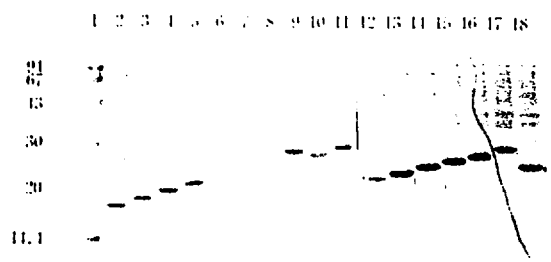
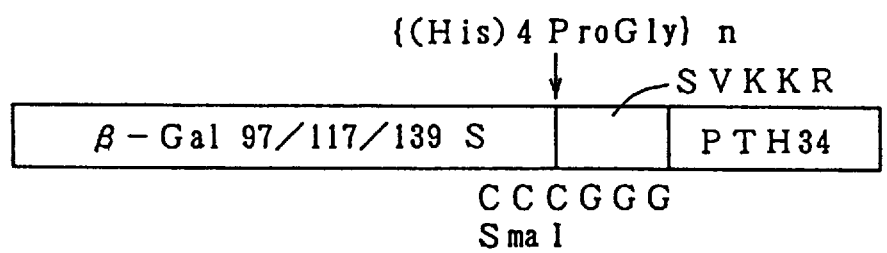
| | | |
|---|---|---|
| 1 STANDARD | 12 | βGal 117S |
| 2 βGal 97S | 13 | βGal 117S 4H |
| 3 βGal 97S 4H | 14 | βGal 117S 8H |
| 4 βGal 97S 8H | 15 | βGal 117S 12H |
| 5 βGal 97S 12H | 16 | βGal 117S 16H |
| 6 βGal 97S 4K | 17 | βGal 117S 24H |
| 7 βGal 97ShANP | 18 | βGal 117S 4K |
| 8 βGal 139S | | |
| 9 βGal 139S 8H | | |
| 10 βGal 139S 4K | | |
| 11 βGal 139S 12H | | |
MOLECULAR WEIGHT OF STANDARD:DESCRIBED IN KD ON THE LEFT END OF THE DRAWING

Fig. 14

(a) GLP1-37[Gly] SYNTHETIC DNA

GLP-1 5'           CG GAA GGT ACC TTT ACC AGC GAT GTG AGC TCG TAT CTG GAA GGT CAG GCG GCA AAA G 3'
GLP-2 3' GTACGC CTT CCA GGT AAA TGG TCG CTA CAC TCG AGC ATA GAC CTT CCA 5'

-GLP-3            5' AA TTC ATC GCG TGG CTG GTG AAA GGC CGT GGT TAA G 3'
GLP-4 3' GTC CGC CGT TTT CTT AAG TAG CGC ACC GAC CAC TTT CCG GCA CCA ATT CAGCT 5'

(b) PCR PRIMER

117S4H Sph I PRIMER
5' TGA ATT TCA GAA GCA TGC CGC TTA TGT CGA GAA GGC CT 3'
                              SphI

117S4H Bgl II PRIMER
5' GAC TCA GAT CTT CCT GAG GCC GAT 3'
          BglII

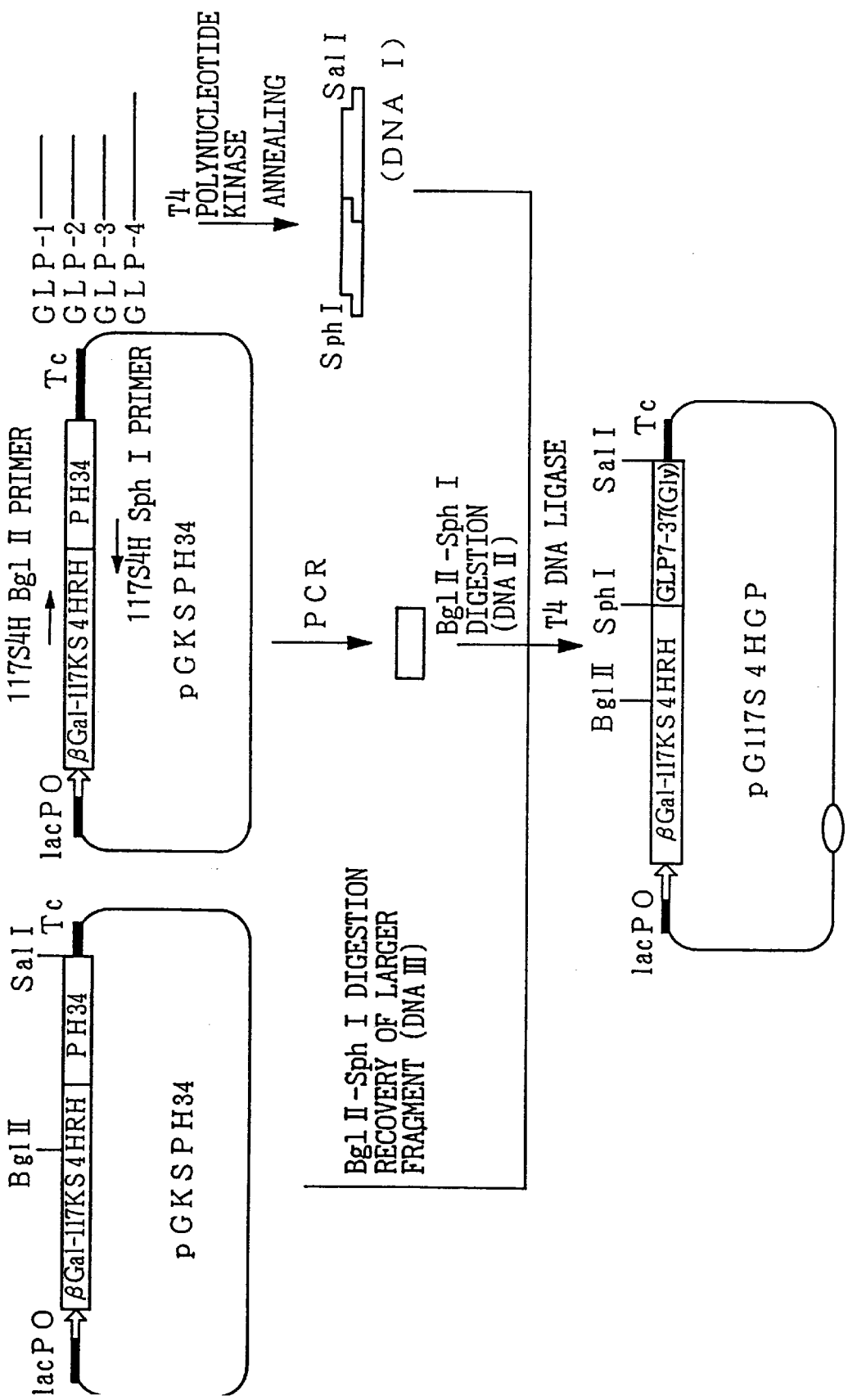

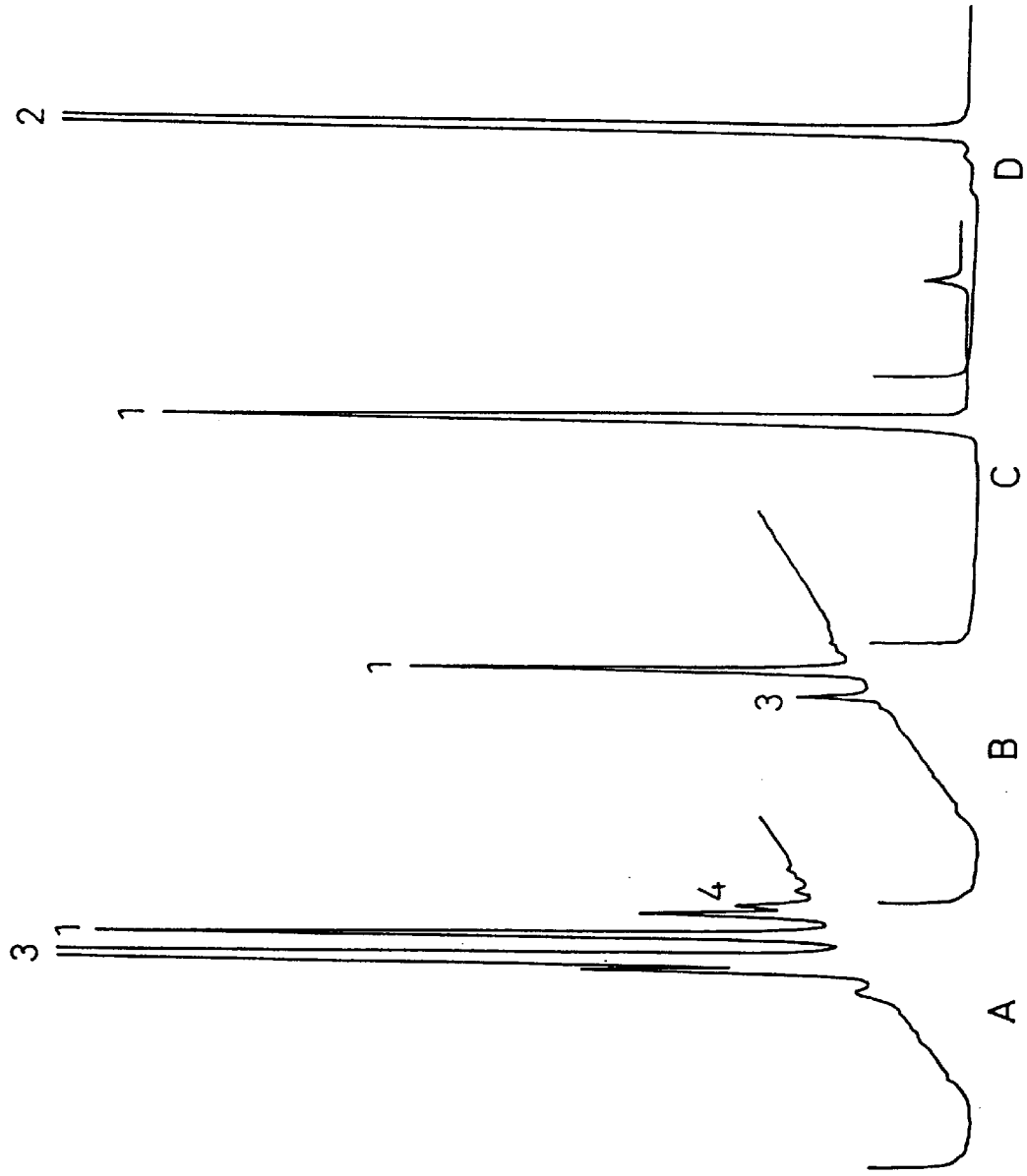

METHOD FOR CLEAVING CHIMERIC PROTEIN USING PROCESSING ENZYME

BACKGROUND OF THE INVENTION

1. Field of the Invention

The present invention relates to a chimeric protein serving as a substrate in the production of a physiologically active peptide or a precursor thereof, and a process for producing the physiologically active peptide or a precursor thereof. Further, the present invention relates to a method for separating the physiologically active peptide from the chimeric protein to purify the physiologically active peptide.

2. Related Art

A number of peptide production processes utilizing the expression of a chimeric protein have been attempted. In this case, chemical or enzymatic cleavage is used for separating a target peptide. Enzymes used in this method include lysyl-endopeptidase (Achromobacter protease I) for specifically cleaving the peptide bond on the C-terminal side of a lysine residue and Staphylococcul protease V8 for specifically cleaving the C-terminal side of a glutamic acid. Chemical methods include cleaving of an asparagine residue by nitrous acid and cleaving of a methionine residue by CNBr.

For the chemical methods, the modification of the target peptide is unavoidable, necessitating the separation of the target peptide from various analogues in the purification of the target peptide after cleaving. On the other hand, for the enzymatic cleaving method, the specificity is high, and the cleaving is performed under relatively moderate conditions, facilitating the purification of the target peptide. Since, however, whether or not enzymes are usable depends upon the amino acid sequence of the target peptide, existing proteases cannot be always used, leading to a demand for universal cleavage enzymes.

When a peptide hormone or a precursor thereof is produced in an organism, a precursor polypeptide for the peptide is specifically cleaved by an enzyme (a processing enzyme). Examples of such enzymes known in the art include a prohormone enzyme 1/3 (PC 1/3), a prohormone enzyme 2 (PC 2), and furin. Kex2 protease which functions in the production of an α-mating factor of *Saccharomyces cerevisiae* is also a kind of the above enzyme. When these processing enzymes are used for excising a target peptide from the chimeric protein, it is expected that the peptide hormone is not damaged and the processing enzymes is applicable to a wide variety of peptides. Therefore, the development of such production methods has been desired in the art.

The present inventors have reported a method which comprises providing a polypeptide, derived from *E. coli* β-galactosidase, as a protective peptide, selecting a proper linker peptide, and efficiently producing a chimeric protein with a target peptide, as an insoluble inclusion body (Japanese Unexamined Patent Publication (Kokai) No. 5-328992). This chimeric protein is solubilized with a modifier, such as urea, and used as a substrate for processing enzymes.

Non-published Art

On the other hand, the present inventors have disclosed a method wherein Kex2 protease derived from *Saccharomyces cerevisiae*, a membrane-bound enzyme, is produced as a soluble enzyme (a secretory Kex2 derivative) by altering the gene (Specification of an application filed on Mar. 4, 1996; title of the invention "Process for Producing Secretory Kex2 Derivative". No design of a chimeric protein as a substrate in the use of this enzyme as a processing enzyme has been referred to in the specification.

SUMMARY OF INVENTION

Accordingly, the development of a method for designing and producing a chimeric protein which can be efficiently produced as an inclusion body in *Escherichia coli* (*E. coli*) under large scale culture conditions and can be easily solubilized under conditions for permitting a processing enzyme to effectively act, and a method for designing and producing an amino acid sequence in the vicinity of the cleaving site so as to enable a target peptide to be efficiently cleaved from the chimeric protein by a processing enzyme, has been desired in the art. Further, the development of a highly versatile method for purifying the produced physiologically active peptide to a purity of not less than 99% has also been desired in the art.

Accordingly, an object of the present invention is to provide a method for designing and producing a chimeric protein serving as a substrate in the production of a physiologically active peptide using a processing enzyme, such as a secretory Kex2 derivative, and to provide a process for purifying the peptide.

The present inventors have made studies with a view to solving the above problems and, as a result, have for the first time clarified that:

1) insertion of a sequence rich in His, for example, a linker peptide containing $\{(His)_4\text{-Pro-Gly SEQ ID NO: }49\}_n$ (n=1 to 6), into a chimeric protein leads to increased production and, in addition, increased solubility under conditions for reacting the chimeric protein with a processing enzyme, such as a secretory Kex2 derivative, 2) a requirement for a highly reactive substrate is such that the amino acid sequence $X_1\text{-}X_2\text{-}(Lys/Arg/Pro)\text{-}Arg$ SEQ ID NO: 50, wherein $X_1$ preferably represents Lys, Arg, or His and $X_2$ preferably represents His or Phe, is used as an amino acid sequence in the linker at its site on which the processing enzyme act, and 3) after the reaction, a series of steps of shifting pH of the reaction solution to the acidic side, diluting the solution to decrease the concentration of the denaturant to permit most of the components other than the target peptide to be precipitated, followed by centrifugation or press filtration enables 95% or more of the target peptide to be recovered in the supernatant, and use of, for example, a cation exchange chromatography, a low-pressure reversed phase chromatography, a reversed phase HPLC and the like, either alone or preferably in combination, enables the target peptide to be purified into a high purity with a high recovery, which has led to the completion of the present invention.

Thus, according to one aspect of the present invention, there is provided a chimeric protein represented by the following formula;

A-L-B wherein A represents a protective peptide;
B represents a target peptide; and
L represents a linker peptide having the sequence $X_1\text{-}X_2\text{-}$(Pro, Lys, or Arg)-Arg, wherein $X_1$ and $X_2$ represent any amino acid, in its C-terminal region and a domain rich in His in its N-terminal region.

Preferably, the domain rich in His at the N-terminal has the sequence: [(His)$_4$-Pro-Gly]$_n$ wherein n is 1 to 6. Further, preferably, X$_1$ represents Arg, Lys, or His, and X$_2$ represents His or Phe. Any 1 to 5 amino acids may exist between the amino acid sequence in the N-terminal region and the amino acid sequence in the C-terminal region.

According to another aspect of the present invention, there is provided a process for producing the above chimeric protein, comprising the steps of:

transforming an expression vector containing DNA encoding the chimeric protein into a host cell;

culturing the resultant transformants; and harvesting the chimeric protein from the culture.

According to a further aspect of the present invention, there is provided a process for producing the above target peptide (B), wherein a processing enzyme is allowed to act on the above chimeric protein to cleave a peptide bond between the C-terminal of the linker peptide (L) and the N-terminal of the target peptide (B) to obtain the target peptide (B).

According to a preferred embodiment of the present invention, the above process comprises the steps of: transforming a vector, capable of expressing a gene encoding a chimeric protein, into a host cell; culturing the resultant transformant; disrupting the transformant to provide an insoluble fraction of an inclusion body; treating the insoluble fraction with a solubilizing agent to solubilize a chimeric protein in the inclusion bodies; cleaving a peptide bond, between the C-terminal of the linker amino acid residue of the solubilized chimeric protein and the N-terminal of the target peptide, by a processing enzyme, such as a secretory Kex2 derivative to separate the target peptide; and purifying the target peptide by precipitation, cation exchange chromatography, low-pressure reversed chromatography, and reversed phase HPLC.

BRIEF DESCRIPTION OF THE DRAWINGS

FIG. 1 illustrates the sequence of a synthetic oligomer used in the preparation of a synthetic hProPTH (1-84) gene.

FIG. 2 is a diagram showing the preparation of a synthetic hProPTH (1-84) gene.

FIG. 4 is a diagram showing the preparation of a plasmid pGP#19 capable of expressing a chimeric protein βGal-139S (FM)PPH84.

FIG. 8 is a diagram showing the results of SDS-PAGE by which the influence of a oligohistidine linker {(His)$_4$-Pro-Gly}$_n$ (n=1 to 6) on the productivity of a chimeric protein has been investigated, wherein 4H represents that the number of histidine residues is 4, that is, n=1. "βGal97S", "βGal139S" and "βGal117S" refer to chimeric proteins wherein the first 97, 139 and 117 amino acids, respectively, at the N terminus of E. coli β-Galactosidase, wherein the cysteines are substituted with serines, are connected to amino acids 1–34 of human parathyroid hormone via a linker peptide comprising Ser-Val-Lys-Lys-Arg ("SVKKR"). The oligohistidine linkers are inserted between the βGal sequences and the Ser-Val-Lys-Lys-Arg linker by inserting DNA encoding the histidine linker into a SmaI restriction site. Samples for SDS-PAGE were produced by (i) transforming plasmids encoding chimeric proteins into E. coli (ii) culturing transformed cells in SB medium for 16 hours, (iii) adjusting cultre turbidity to an OD 660 of 10, (iv) adding an equal amount of SDS sample buffer to 100 μl of each cell suspension, and (v) boiling each mixture for 3 minutes. Protein bands in each lane represent the relative amounts of protein present in 10 μl of each sample.

FIG. 14 shows nucleotide sequences of synthetic oligonucleotides for construction of hGLP-1(7-37) gene (DNA (11), and nucleotide sequences of PCR primers using pGKSPH34 as a template.

FIG. 15 shows a process for construction of plasmid pG117S4HGP.

FIG. 16 shows profiles of purification of hGLP-1, wherein A shows a result a sample after reaction with Kex2, B shows a result for a supernatant from acid precipitation, C shows a result for a sample after cation exchange column chromatography and D shows a result for a sample after a low pressure reversed-phase column chromatography. Peak 1 shows hGLP-1(7-37), peak 2 shows hGLP-1, peak 3 shows a protective peptide and peak 4 shows chimeric protein.

DETAILED DESCRIPTION

Figure 3:
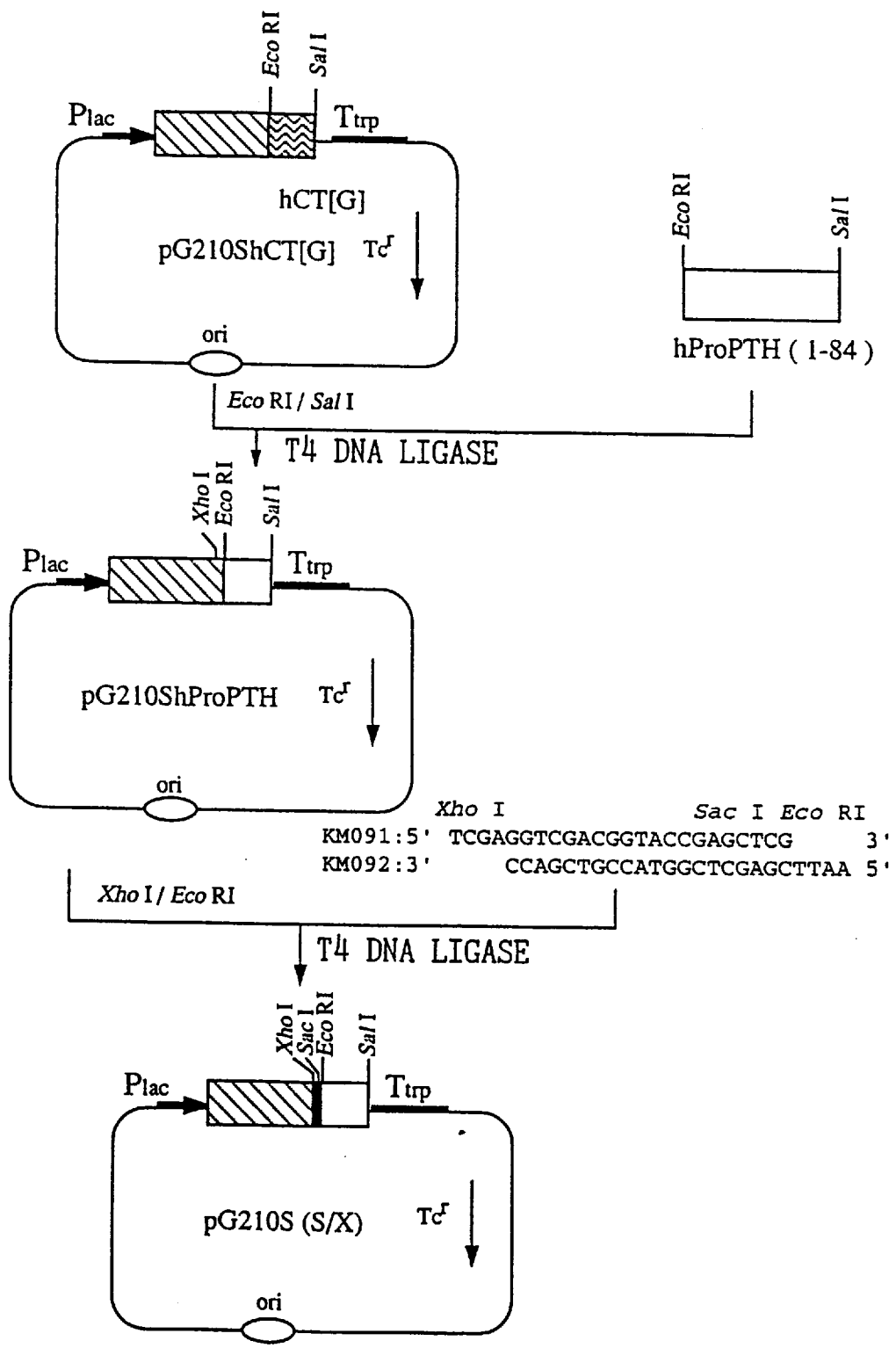
FIG. 3 is a diagram showing the preparation of a plasmid pG210S (S/X), wherein Plac represents a promoter for a lactose operon of E. coli, Ttrp represents an attenuator terminator for TrpE of E. coli.

According to the method of the present invention, the above chimeric protein comprising a protective peptide, a linker, and a physiologically active peptide (a target peptide) can be cleaved by a processing enzyme to produce a physiologically active peptide. Examples of such peptides include, but are not limited to, human parathyroid hormone (hPTH (1-84)) and derivatives thereof (hPTH (1-34), hPTH (1-37), and hPTH (1-38)), other derivatives of human parathyroid hormones (hPTH (1-31) Gly, hPTH (1-34) Gly, hPTH (1-37) Gly, hPTH (1-38) Gly, hPTH (3-84), hPTH (3-34), hPTH (3-37), and hPTH (3-38)), cell growth factors, calcitonin and precursors thereof, glucagon-like peptide 1 (GLP-1) and derivatives thereof (GLP-1 (1-37), GLP-1 (7-37), GLP-1 (7-36) $NH_2$ and the like).

Processing enzymes usable herein include, but are not limited to, Kex2 protease, furin, prohormone convertase 1 (PC1) or prohormone convertase 2 (PC2), or derivatives thereof. In the present invention, secretory Kex2 derivatives prepared by removing the C-terminal hydrophobic region of Kex2 protease are particularly preferred.

The protective peptide according to the present invention is preferably a peptide having a size of not more than 220 amino acids. For example, a peptide of 90 to 210 amino acids counting from the 1-position of the N-terminal of *E. coli* β galactosidase is preferred. More preferred are a peptide of amino acids 1-97, 1-117, or 1-139 on the N-terminal side of *E. coli* β-galactosidase. The above peptides with the cysteine residue being substituted by a serine residue are still more preferred. The above peptides with the arginine residue at the 14-position being substituted by a lysine residue is most preferred. Further, preferably, the protective peptide does not contain a sequence recognizable by a processing enzyme, for example, Pro-Arg, Arg-Arg or Lys-Arg. If the recognition sequence is contained in the protective peptide, the substitution of at least one amino acid in the above recognition sequence with a different amino acid to render the sequence unrecognizable by the processing enzyme can prevent cleaving by the processing enzyme.

The linker amino acid for improving the solubility of the chimeric protein is preferably hydrophilic. Some target peptides cause a change in charge of the chimeric protein, resulting in lowered productivity of the inclusion body. The hydrophilic amino acid is preferably a histidine residue having a buffering property around physiological pH (neutral) within bacteria which are a place for producing inclusion bodies. Further, insertion of the sequence Pro-Gly after denaturation and solubilization is preferred from the viewpoint of moderating the secondary structure of the linker portion. In order to cope with a variety of physiologically active peptides, it is most preferred that a synthetic DNA fragment encoding $(His)_4$-Pro-Gly be provided and properly inserted into a duplicate manner into a DNA fragment encoding a protective peptide to design a linker of $\{(His)_4\text{-Pro-Gly}\}_n$ wherein n=1 to 6. The sequence of the N-terminal portion of this linker will be hereinafter referred to as "LN."

Further, the present inventors have for the first time clarified that the Kex2 protease derivative (secretory Kex2 derivative) derived from *Saccharomyces cerevisiae*, which has become mass-producible, when a chimeric protein is used as a substrate, an amino acid in the vicinity of the Kex2 protease recognition site (Lys/Arg/Pro)-Arg also greatly affects the activity. Specifically, they have clarified that when the amino acid sequence located at the C-terminal of the linker is $X_1$-$X_2$-(Lys/Arg/Pro)-Arg, wherein $X_1$ and $X_2$ represent any amino acid, provided that $X_1$ is Arg, Lys, or His and $X_2$ is His or Phe, the activity of the secretory Kex2 derivative becomes maximum. The sequence of the C-terminal portion of this linker will be hereinafter referred to as "LC."

The target peptide produced and excised by the chimeric protein method may be purified by various methods. In this case, the use of the above chimeric protein has been found to permit the chimeric protein remaining unreacted, the protective peptide, and impurities derived from *E. coli* to be efficiently removed by a simple precipitation procedure. Specifically, it has been found that, after the reaction with the secretory Kex2 derivative, shifting of pH to the weakly acidic side followed by dilution of the reaction solution to decrease the denaturant concentration enables not only most of impurities derived from *E. coli* but also not less than 95% of the chimeric protein remaining unreacted and the protective peptides to be transferred into the precipitate, permitting not less than 95% of the target peptide to stay in the supernatant and a clear liquid containing the target peptide to be simply obtained by centrifugation or press filtration.

After pH adjustment or the like, the supernatant was directly passed through a cation exchange chromatograph to adsorb the target peptide, the target peptide was then eluted by taking advantage of a change in salt concentration or a change in pH, the eluate was passed through a low-pressure reversed phase chromatography to adsorb the target peptide which was then eluted by taking advantage of a change in concentration of an organic solvent followed by concentration of the eluate. After lowering the concentration of the organic solvent, the eluate was subjected to reversed phase HPLC, separation and fractionation were performed by taking advantage of a change in concentration of the organic solvent to give a high-purity target peptide.

The present invention will be described by taking, by way of example, a human parathyroid hormone derivative hPTH (1-34) as a target peptide.

Figure 6:
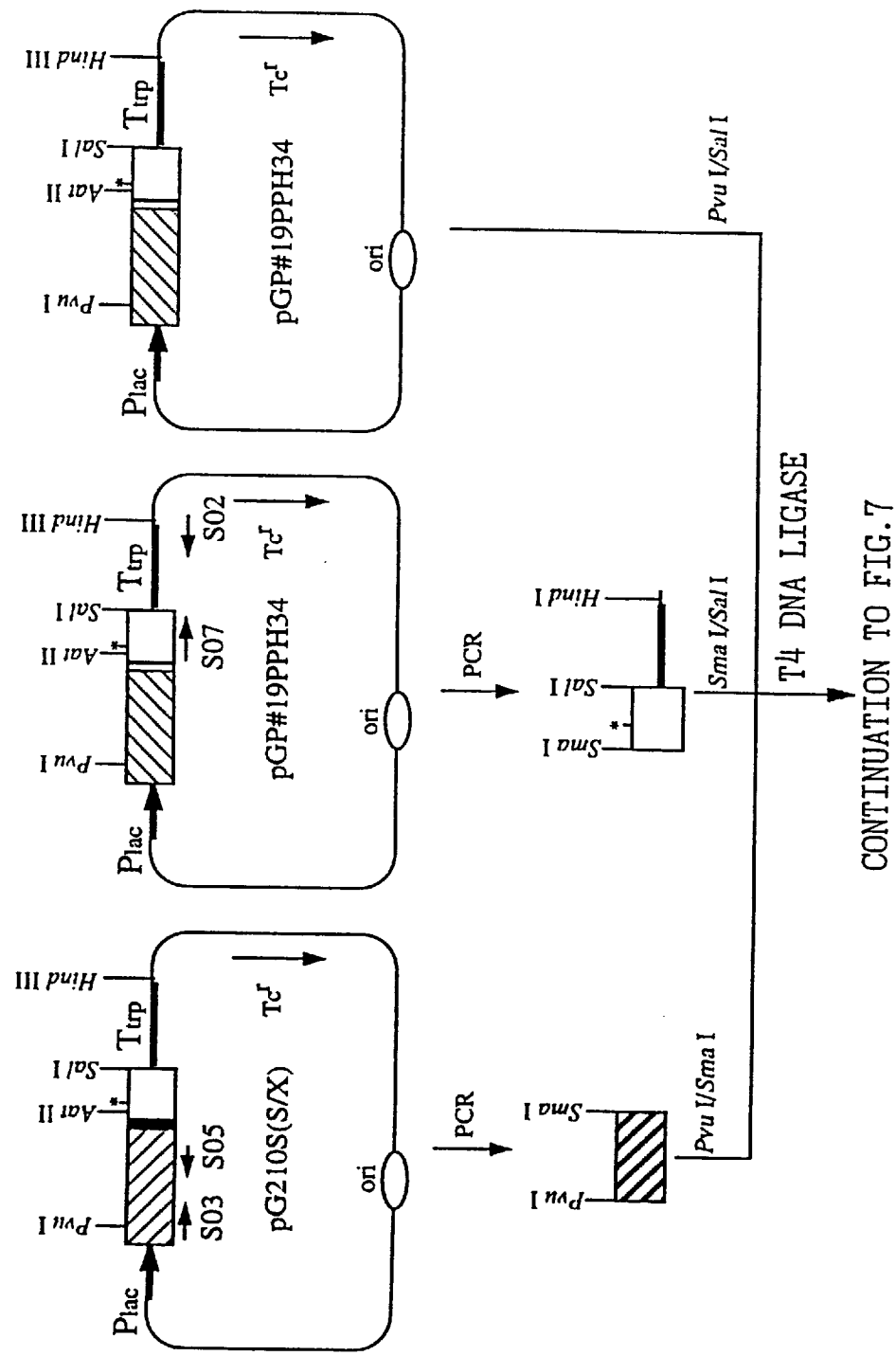
FIG. 6 is a diagram showing the first half of a process for producing plasmids pG117SPPH34 and pG117SnHPPH34 capable of expressing chimeric proteins βGal-117SPPH34 and βGal-117SnHPPH34 (n=1 to 6), wherein pG97SPPH34 and pG97SnHPPH34 were prepared by substituting the primer S04 for the primer S05 and pG139SPPH34 and pG139SnHPPH34 were prepared by substituting the primer S06 for the primer S05.
Figure 7:
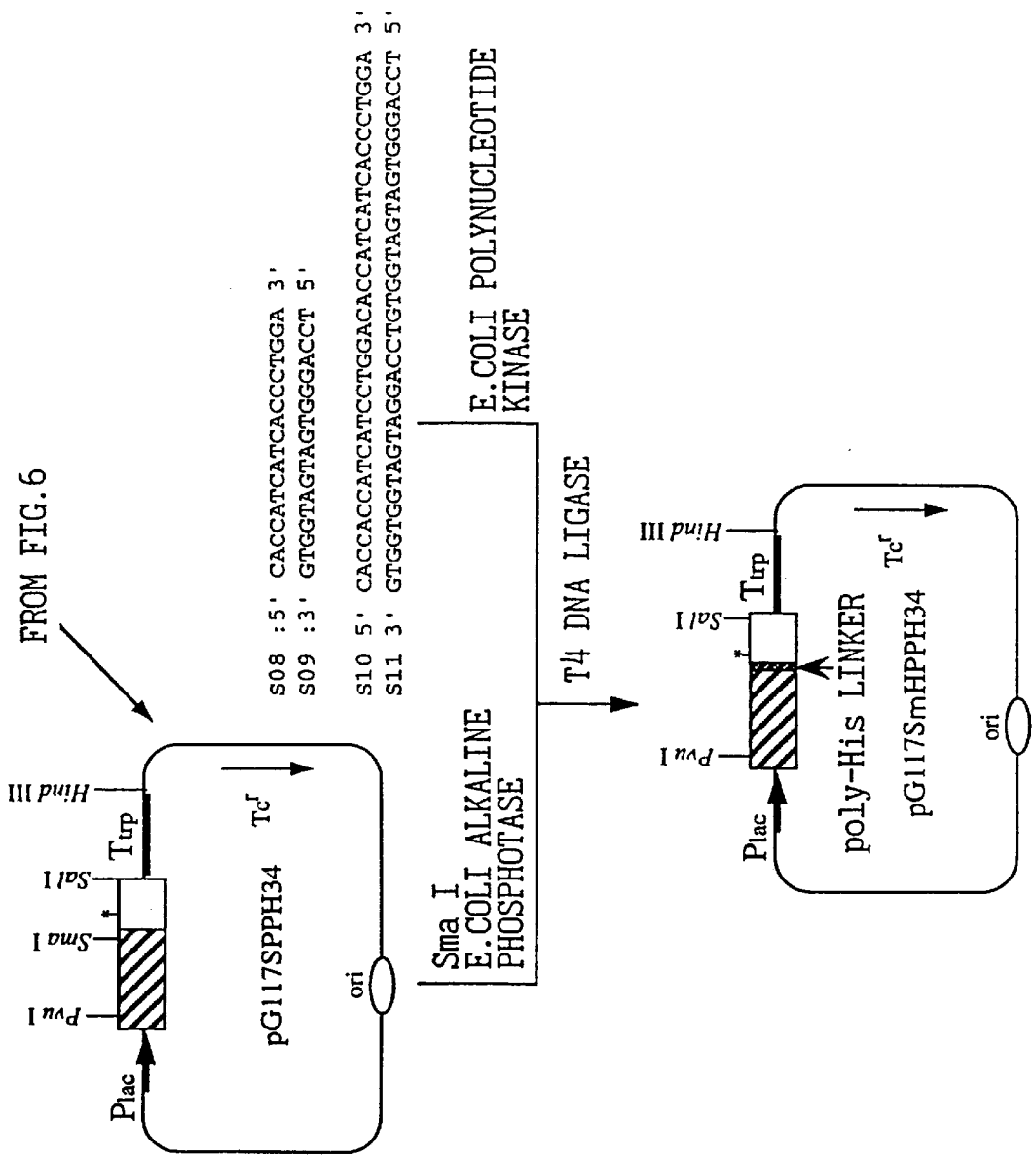
FIG. 7 is a diagram showing the second half of a process for producing plasmids pG117SPPH34 and pG117SnHPPH34 capable of expressing chimeric proteins βGal-117SPPH34 and βGal-117SnHPPH34 (n=1 to 6), wherein pG97SPPH34 and pG97SnHPPH34 was prepared by substituting the primer S04 for the primer S05 and pG139SPPH34 and pG139SnHPPH34 were prepared by substituting the primer S06 for the primer S05.

A βGal-210SPPH84 expression plasmid pG210ShProPTH was prepared by ligating synthetic DNA oligomers together to prepare an hPTH (1-84) gene and substituting the gene thus prepared for a plasmid pG210ShCT[G] in its region encoding hCT[G] (FIG. 3). There was prepared a pG117SHPPH34 wherein a translation stop codon was substituted for a codon encoding an amino acid (Val) located at the 35-position from the N-terminal of an hPTH (1-84) gene and a gene encoding βGal-117S (a peptide of amino acids 1-117 on the N-terminal side of *E. coli* β-galactosidase with the cysteine residue being substituted with a serine residue) was substituted for a gene coding for βGal-210S (a peptide of amino acids 1-210 on the N-terminal side of *E coli* β-galactosidase with the cysteine residues being substituted with the serine residues (FIGS. 6 and 7).

pG139SHPPH34 or pG97SHPPH34 can be prepared in the same manner as described above, except that a gene encoding βGal-139S or a gene encoding βGal-97S is inserted instead of βGal-210S.

In these plasmids, structural genes respectively encoding βGal-97S, βGal-117S, and βGal-139S are connected to a structural gene of a hPTH (1-34) through a linker peptide Phe-Met-Lys-Ser-Val-Lys-Lys-Arg SEQ ID NO: 51, and the structural gene encoding this chimeric protein is under control of a lac promoter. Further, this plasmid contains a tetracycline-resistant gene marker.

βGal-97SPPH34 had low productivity although it had high solubility in a urea solution. On the other hand, for βGal-117SPPH34 and βGal-139SPPH34, although the productivity was high, the solubility under conditions for a reaction with the secretory Kex2 derivative was so low that the use of a larger amount of the secretory Kex2 derivative was necessary for excising the hPTH (1-34) from the chimeric protein. For this reason, a linker LN, which is hydrophilic, exhibits a buffering property around pH 7 (neutral) and comprises amino acids capable of inhibiting the formation of a secondary structure of the chimeric protein, was inserted between the protective peptide and the linker Met-Ser-Val-Lys-Lys-Arg, in order to provide a chimeric protein having high productivity and high solubility in a urea solution.

A peptide having the sequence $\{(His)_4\text{-Pro-Gly}\}_n$, wherein n=1 to 6, was used as LN. $\{(His)_4\text{-Pro-Gly}\}_n$, wherein n=1 to 6, is introduced by synthesizing a DNA fragment encoding $(His)_4$-Pro-Gly or $\{(His)_4\text{-Pro-Gly}\}_2$ and inserting the DNA fragment into the 3'-terminal portion of a DNA fragment encoding the protective peptide in a suitable molar ratio. Thus, a gene can be prepared which encodes a chimeric protein comprising a linker peptide containing one or a plurality of the above amino acid sequences.

Figure 9:
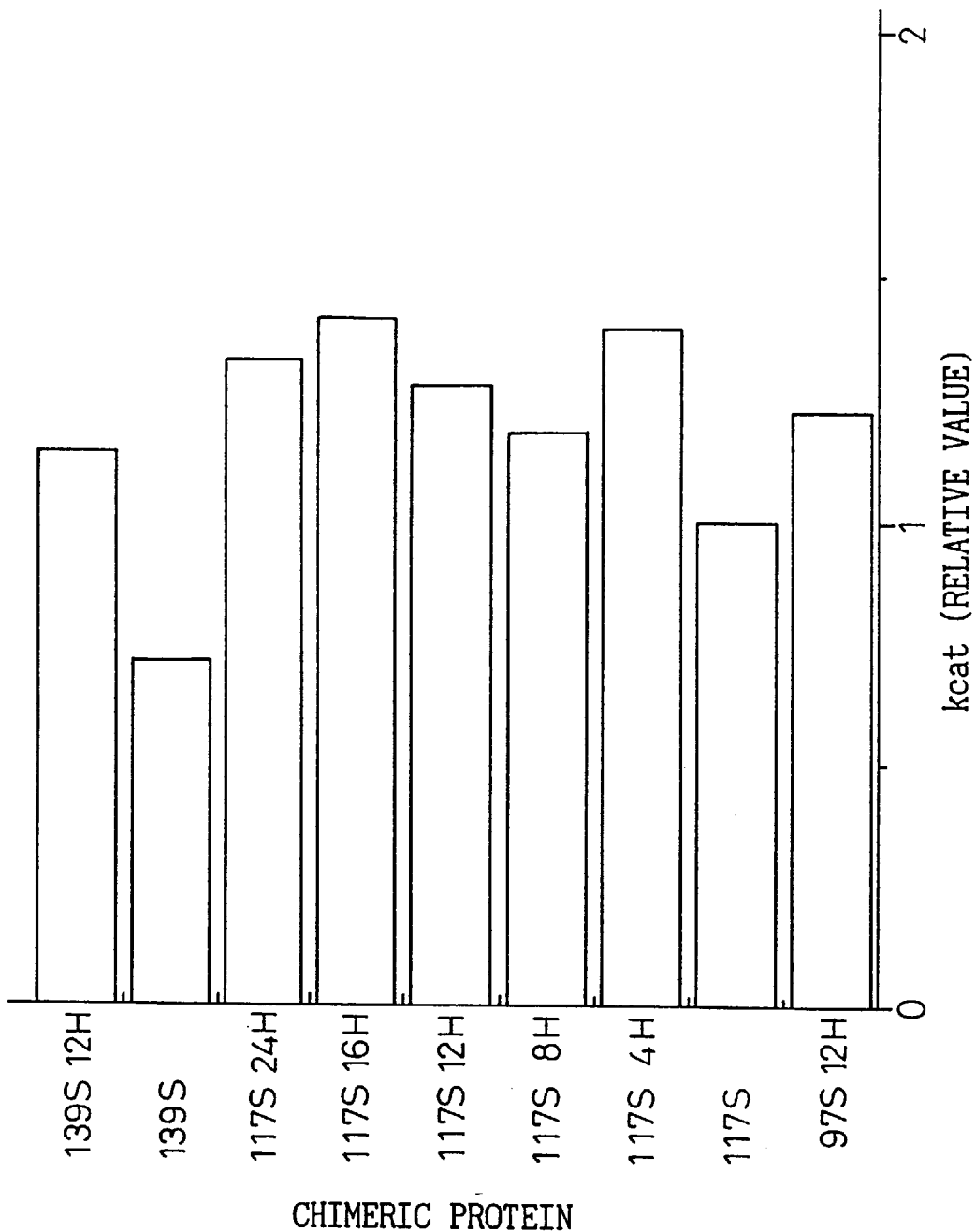
FIG. 9 is a diagram showing the influence of a polyhistidine linker {(His)$_4$-Pro-Gly}$_n$ (n=1 to 6) on the efficiency of the cleavage of hPTH(1-34) by Kex2-660, wherein the abscissa represents the relative kcat value when the kcat value of βGal-117SPPH34 is equal to 1. Kcat values were determined as follows. The amount of target peptide following cleavage with Kex2-660 at intervals was quantified by (i) applying the sample supernatants to HPLC and comparing the area of hPTH(1-34) peaks to a standard control at an absorbance of 214 nm, (ii) plotting the concentration of the target peptide against sampling intervals and obtaining an initial velocity, and (iii) dividing each velocity by the velocity for βGal 117S.

A gene with a DNA fragment inserted in a reversal state was confirmed by DNA sequencing and excluded. E. coli strain M25 was transformed with plasmids encoding chimeric proteins to examine the productivity of the chimeric proteins (FIG. 8). As a result, it was found that in the case of the protective peptides βGal-97S and βGal-139S, n=3 offered high productivity of the chimeric protein, while in the case of the protective peptide βGal-117S, n=1 to 6 offered high productivity of the chimeric protein. Inclusion bodies of these chimeric proteins were subjected to cell disruption and centrifugation to conduct washing and separation, solubilized with urea, diluted and used for a reaction with Kex2-660 (FIG. 9)

As a result, it was found that the introduction of $\{(His)_4\text{-Pro-Gly}\}_n$, wherein n=1 to 6, enhanced the sensitivity of all the chimeric proteins to Kex2-660. Accordingly, for the chimeric protein for the production of hPTH (1-34), βGal-117S4HPPH34 comprising βGal-117S as the protective peptide and $(His)_4$-Pro-Gly as the linker peptide LN were adopted by taking into consideration the productivity of the chimeric protein, the reactivity with Kex2-660, and the size of the protective peptide.

The above results show that, in the design of a chimeric protein for excising a physiologically active peptide by a secretory Kex2 derivative, the insertion of a peptide of $\{(His)_4\text{-Pro-Gly}\}_n$, wherein n=1 to 6, is suitable for improving not only the productivity in E. coli but also the solubility under conditions for a reaction with a secretory Kex2 derivative.

In the present process, the secretory Kex2 derivative should be used in an amount of about 1:1000 in terms of the molar ratio to the chimeric protein and, hence, occupies the major part of the cost of raw materials for the production. Therefore, this has required a design of a chimeric protein which can be more easily cleaved by the secretory Kex2 derivative. A pro-sequence Lys-Ser-Val-Lys-Lys-Arg of a precursor to a human parathyroid hormone was used for the secretory Kex2 derivative recognition site of βGal-117S4HPPH34. However, whether or not this sequence is best suited for cleaving by the secretory Kex2 derivative is unknown, and there is a possibility that, like many other proteases, optimization results in further increased cleaving efficiency. Since hPTH(1-34) is connected to the recognition site on its C-terminal side, the substitution of the amino acid cannot be conducted, whereas the sequence on the N-terminal side can be freely selected so far as no recognition site is newly created. Accordingly, an attempt was made to covert the P3-site ($X_2$) of the chimeric protein as a substrate to any amino acid. Studies have been made on 18 amino acid sequences shown in FIG. 10. As a result, it was found that the introduction of His or Phe into $X_2$ permits hPTH (1-34) to be excised from the chimeric protein with improved efficiency.

Figure 11:
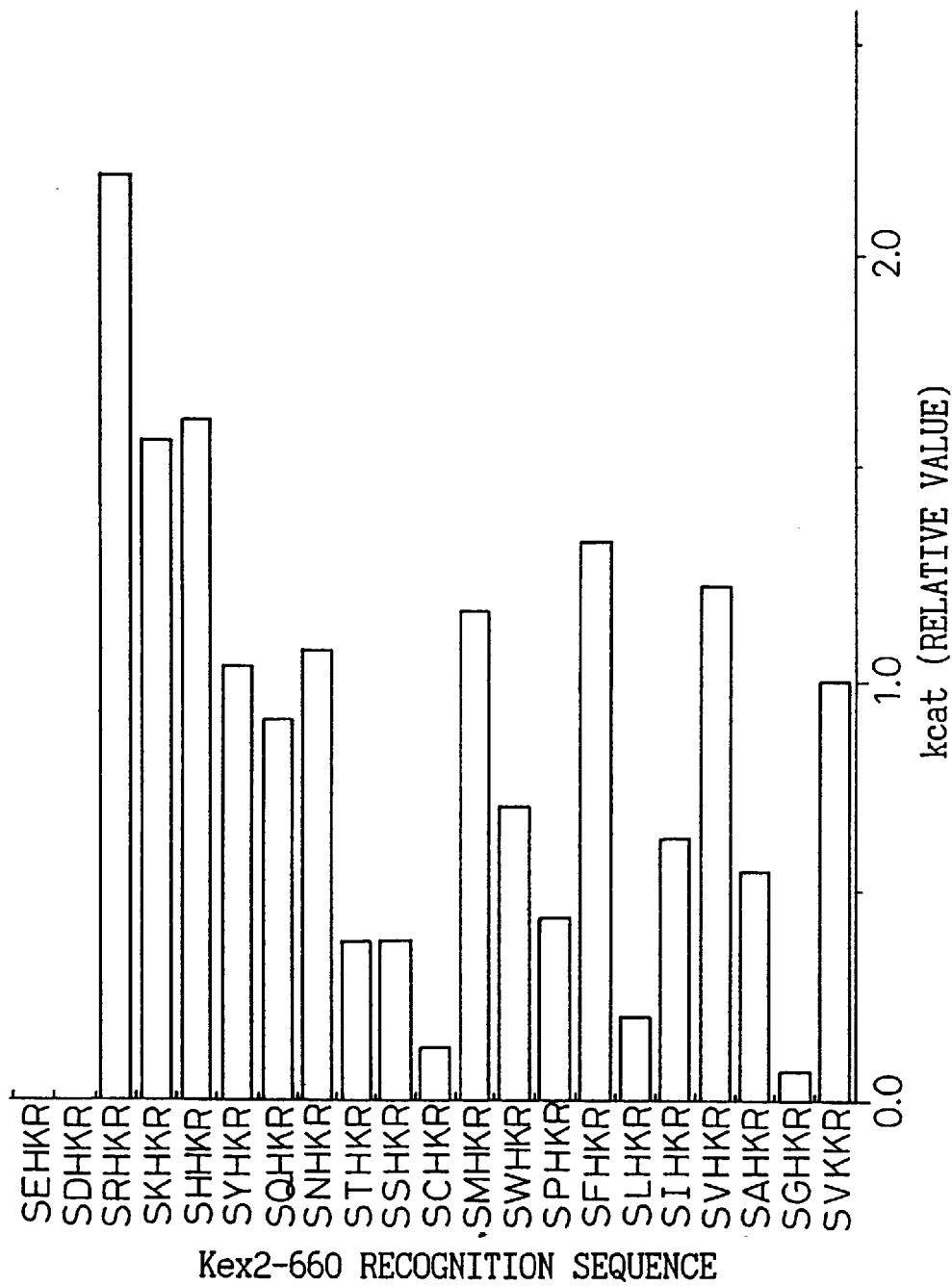
FIG. 11 is a diagram showing the influence of an amino acid at Kex2 protease recognition site P4 on the efficiency of the cleavage of hPTH (1-34) by Kex2-660, the amino acid at the site P3 being immobilized onto a histidine residue with the amino acid at the site P4 being substituted, wherein the abscissa represents the relative kcat value with the kcat value of βGal-117S4HVKPH34 being supposed to be 1.

Thereafter, studies have been made on the P4 site using 20 amino acid sequences shown in FIG. 11 with His, which exhibited no significant side reaction, immobilized onto $X_2$. As a result, it was found that the introduction of Arg, Lys, or His into $X_1$ permits hPTH (1-34) to be excised from the chimeric protein with higher efficiency. Arg-His-Lys-Arg which had offered the highest cleavage efficiency was selected as LC.

Further, in the course of the present studies, it was found that the peptide bond on the C-terminal side of the sequence Arg-Arg present at the 13- and 14-positions of βGal-117S is cleaved by a secretory Kex2 derivative and, consequently, in the subsequent step of purification by precipitation with an acid, the resultant βGal (1-14) is recovered in the supernatant fraction with hPTH (1-34) too being recovered therein. Therefore, Lys was substituted for 14 Arg to inhibit the cleaving, thereby preventing the production of βGal(1-14).

Based on the above results, for the chimeric protein for the production of hPTH (1-34), βGal-117S (βGal-117KS) with 14 Arg being substituted with Lys was adopted as the protective peptide, and a peptide having an amino acid sequence of Pro-His-His-His-His-Pro-Gly-Gly-Arg-Pro-Ser-Arg-His-Lys-Arg SEQ ID NO: 52 was adopted as a linker peptide.

The present inventors expressed the chimeric protein βGal-117KS4HRHPH34, thus designed, in E. coli, the resultant inclusion body was washed, recovered, solubilized, and used for a reaction with a secretory Kex2 derivative, followed by studies on a purification method. As a result, a peptide containing impurities derived from E. coli, chimeric protein remaining unreacted, and protective peptide could be precipitated by utilizing a phenomenon wherein a shift of pH from neutral to the weakly acidic side causes a marked lowering in solubility, that is, by shifting pH from 7.8 to 8.2, an optimal pH for a reaction with a secretory Kex2 derivative, to 6.2 to 6.5.

Further, decreasing the denaturant (urea) concentration by dilution enabled most of the impurities to be precipitated. The precipitate was removed by centrifugation or press filtration to efficiently recover hPTH (1-34) in the supernatant. The supernatant was adjusted to pH 5.0 and passed through a cation exchange chromatography (for example, PorosHS, SP Toyopearl) to adsorb hPTH (1-34), followed by elution with 0.3–0.4M NaCl. Acetic acid was added to the eluate, the mixed solution was then passed through a low-pressure reversed phase chromatography (for example, PorosR2, SokenODS-W) to adsorb hPTH(1-34), followed by elution with about 30% acetonitrile to remove impurities which adversely affect concentration and reversed phase HPLC.

The acetonitrile contained in the eluate was distilled off under reduced pressure, and the residue was filtered through a 0.22 μm filter, passed through reversed phase HPLC (for example, InertsiliPrepODS, TSK-ODS-120T) to adsorb hPTH(1-34), and fractionated by gradient elution of acetonitrile. A high-purity fraction was collected. Thus, hPTH(1-34) having a purity of 99.5% was fractionated with a recovery of 40 to 70%. The above results show that this recovery is the highest one among those reported in the art, substantiating the usefulness of the present invention.

EXAMPLES

The present invention will be described in more detail with reference to the following example, though it is not limited to these examples only.

At the outset, plasmid and *E. coli*, used as materials for the present invention, and basic experimental procedures common to each example will be described.

Plasmid

A plasmid pG210ShCT[G] is a plasmid which can express, under the control of a promoter of *E. coli* lactose operon (a lac promoter), a chimeric protein comprising a peptide of amino acids 1-210 on the N-terminal side of β-galactosidase with 76 Cys, 122 Cys, and 154 Cys being substituted by Ser, i.e., βGal-210S, and hCT [G] (a peptide of human calcitonin with a glycine residue added to the C-terminal of the amino acid 32) bound to βGal-210S through a glutamic acid residue.

Figure 13:
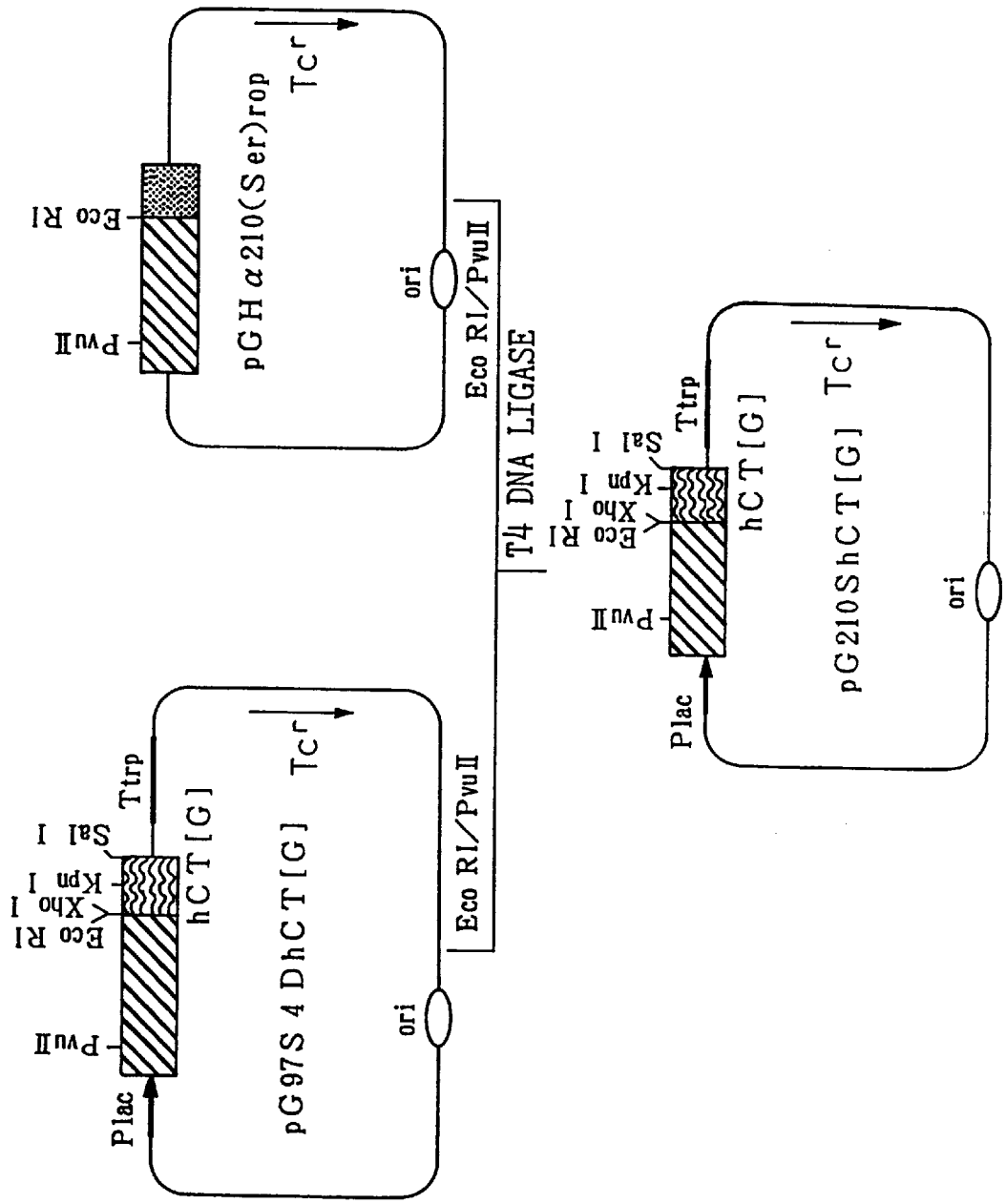
FIG. 13 is a diagram showing the preparation of a plasmid pG210ShCT(G).

It was prepared by ligating a DNA fragment comprising a gene encoding a part of βGal-210S, the DNA fragment being prepared by digesting pGHα210 (Ser)rop$^-$ with restriction enzymes PvuII and EcoRI, with a DNA fragment comprising a vector prepared by digesting pG97S4DhCT[G] with restriction enzymes PvuII and EcoRI (FIG. 13). A process for preparing pGHα210(Ser)rop$^-$ is disclosed in Japanese Examined Patent Publication (Kokoku) No, 6-87788, and *E. coli* strain W3110 containing the plasmid pG97S4DhCT[G] was designated as "*Escherichia coli* SBM 323," and deposited as FERM BP-3503 with Institute of Bioscience and Human Technology Agency of Industrial Science and Technology, Ministry of International Trade & Industry on Aug. 8, 1991.

Introduction of a DNA region, encoding a target peptide, as an EcoRI-SalI DNA fragment into plasmid pG210ShCT[G] while matching the reading frame enables the expression of a chimeric protein with βGal-210S. The plasmid was used for cloning of a synthetic human parathyroid hormone (hProPTH (1-84)) gene and as a material for the preparation of plasmid pGP#19 (FIG. 3).

*Escherichia coli* (*E. coli*)

*E. coli* strain JM109 was purchased as a competent cell from Toyobo Co., Ltd. and used in the preparation of a plasmid. *E. coli* strain M25 (W3110/ompT: Sugimura et al. Biochem. Biophys. Res. Commun., 153, 753–759, 1988) was utilized in the expression of a chimeric protein.

Medium

The following media was used in the culture of *E. coli*.

SB medium: 0.5% (w/v) glycerol, 2.4% (w/v) yeast extract, 1.2% (w/v) trypton, 0.1M potassium hydrogenphosphate buffer (pH 7.5).

NU1 synthetic medium: 0.4% (w/v) yeast extract, 0.4% (w/v) $K_2HPO_4$, 0.4% (w/v) $KH_2PO_4$, 0.27% (w/v) $Na_2HPO_4$, 1.2% (w/v) $(NH_4)_2SO_4$, 0.02% (w/v) $NH_4Cl$, 0.3% (w/v) L-methionine, 0.2% (w/v) $MgSO_4.7H_2O$, 40 mg/L $FeSO_4.7H_2O$, 40 mg/L $CaCl_2.2H_2O$, 10 mg/L $AlCl_3.6H_2O$, 10 mg/L $CoCl_2.6H_2O$, 2 mg/L $ZnSO_4.7H_2O$, 2 mg/L $Na_2MO_4.2H_2O$, 1 mg/L $CuCl_2.2H_2O$, 0.5 mg/L $H_3BO_3$, and 10 mg/L $MnSO_4.nH_2O$.

Basic Experimental Procedures

In the examples, the following experimental procedure was used unless otherwise specified.

DNA primers were synthesized with a automatic synthesizer (Model 320 A, manufactured by Applied Biosystems) by the phosphoamidite method. The DNA sequence was determined by the dideoxy method.

DNA cleavage was performed by a reaction using a restriction enzyme (amount: 3 to 10 folds) indicated by the supplier for one hr. The structure of the plasmid was analyzed using 0.5 to 1 μg of DNA in 20 μl of a reaction solution, and the preparation of DNA was performed using 3 to 10 μg of DNA in 50 to 100 μl of a reaction solution. The reaction temperature, the reaction buffer and other conditions were as indicated by the supplier.

A sample for electrophoresis on agarose gel was prepared by adding 0.2 volume of a dye (a 15% (w/v) aqueous Ficoll solution containing 0.25% (w/v) bromphenol blue) to the reaction solution. TAE buffer (40 mM Tris/acetic acid, 2 mM EDTA) was used as a buffer for electrophoresis on agarose gel. For the structural analysis of a plasmid, electrophoresis at 100 V for one hr was performed using Mupid-2 (manufactured by Cosmo-Bio Co., Ltd.), and for the preparation of DNA, electrophoresis was performed on a horizontal gel (20 cm×15 cm×0.7 cm) at 150 V for 4 hr or at 35 V for 13 hr. The gel was stained with an aqueous ethidium bromide solution (0.5 μg/ml) for 20 min and irradiated with ultraviolet light to detect a DNA band. The agarose gel concentration was 1.0% or 2.0% (w/v) depending upon the size of the DNA fragment to be fractionated.

DNA in the agarose gel was extracted from the agarose gel by placing the gel in a dialysis tube filled with 0.1× TAE buffer and applying a voltage to conduct elution. The DNA solution was treated with phenol and chloroform and subjected to precipitation with ethanol to purify DNA.

Ligation was performed by adding 10 units of T4 DNA ligase to 30 μl of a reaction solution (67 mM Tris/HCl (pH 7.5), 5 mM $MgCl_2$, 5 mM DTT, 1 mM ATP) containing 0.05 to 1 μg of a DNA fragment and allowing a reaction to proceed at 16° C. for 12 to 18 hr or by using TAKARA Ligation Kit (manufactured by Takara Shuzo Co., Ltd.).

*E. coli* strain JM109 was transformed as indicated by the supplier, *E. coli* strain M25 was transformed by the calcium chloride method, and the transformed strain was selected by taking advantage of drug resistance (tetracycline).

An SDS-polyacrylamide gel electrophoresis (SDS-PAGE) sample was prepared by adding the same amount of SDS sample buffer (63 mM Tris/HCl (pH 6.8), 10% (w/v) glycerol, 10% (w/v) SDS, and 10 μg/ml bromophenol blue) and boiling the mixture for 3 min. The electrophoresis was performed on 16% (w/v) SDS-PAGE mini (TEFCO) gel at 20 mA per piece of gel for 70 min, and the gel was stained with Coomassie Brilliant Blue G.

hPTH(1-34) was quantitatively determined by first subjecting a solution containing hPTH (1-34) to 10- to 20-fold dilution with a sample buffer (1M acetate/2M urea), centrifuging the diluted solution to obtain a supernatant, applying the supernatant to HPLC (LC10A, manufactured by Shimadzu Seisakusho Ltd.) to which YMC-ODS-A302 (d4.6 mm×150 mm) column (manufactured by K.K. Yamamura Kagaku Kenkyujo) has been connected, conducting development using liquid A (0.1% (v/v) trifluoroacetic acid (TFA) /10% (v/v) acetonitrile) and liquid B (0.094% (v/v) TFA/ 50% (v/v) acetonitrile) with gradient B 40%→80%/20 min, and comparing the area of a hPTH (1-34) peak, detected by determination of absorbance at 214 nm, with a peak area of standard hPTH (1-34) having a known concentration.

Other basic gene manipulation was performed according to a method described in Molecular Cloning (Maniatis, et al., Cold Spring Harbor Laboratory, New York (1982)) unless otherwise specified.

Example 1
Preparation of hProPTH (1-84) Gene

As shown in FIG. 1, hProPTH (1-84) gene was synthesized as 14 divided fragments of U1 to U7 (SEQ ID NOS: 1 to 7) and L1 to L7 (SEQ ID NOS: 8 to 14).

These fragments were ligated as described below to prepare hProPTH (1-84) gene (FIG. 2).

At the outset, about 1 μg of DNA fragments U1 (SEQ ID NO: 1) and about 1 μg of DNA fragment L7 (SEQ ID NO: 14) were reacted in 15 μl of a phosphorylation solution (50 mM Tris/HCl (pH 7.6), 10 mM MgCl$_2$, 5 mM DTT) containing 16 units of T4 polynucleotide kinase and 0.5 nM (1 MBq or more) [γ-$^{32}$P]dATP at 37° C. for 15 min. 5 μl of a phosphorylation solution containing 5 mM ATP was added thereto, and a reaction was allowed to proceed at 37° C. for 45 min. The same procedure was repeated for a combination of U2 (SEQ ID NO: 2) with L6 (SEQ ID NO: 13), a combination of U3 (SEQ ID NO: 3) with L5 (SEQ ID NO: 12), a combination of U4 (SEQ ID NO: 4) with L4 (SEQ ID NO: 11), a combination of U5 (SEQ ID NO: 5) with L3 (SEQ ID NO: 10), a combination of U6 (SEQ ID NO: 6) with L2 (SEQ ID NO: 9), and a combination of U7 (SEQ ID NO: 7) with L1 (SEQ ID NO: 8).

The above 7 reaction solutions were combined, and the resultant mixture was subjected to precipitation with ethanol to recover DNA which was then dissolved in 80 μl of 100 mM Tris/HCl (pH 7.6), 6.5 mM MgCl$_2$, and 300 mm NaCl. A 40 μl aliquot was allowed to stand at 95° C. for 5 min, and the temperature was then decreased to 43° C. over a period of 30 min. It was then ice cooled, 40 μl of ligation liquid B (manufactured by Takara Shuzo Co., Ltd.) was added thereto, and the mixture was allowed to stand at 26° C. for 15 min.

This sample was electrophoresed on 5% polyacrylamide. After the electrophoresis, a ligated DNA fragment was detected by autoradiography. A DNA fragment corresponding to about 280 bp was extracted from the gel and then purified by a conventional method.

Example 2
Preparation of βGal-139S(FM)PPH84 Expression Plasmid pGP#19

The about 280 bp DNA fragment containing a synthetic hProPTH (1-84) has a restriction enzyme EcoRI site at the 5'-terminal and a restriction enzyme SalI site at the 3'-terminal. Cloning of the hProPTH (1-84) gene was performed by inserting the EcoRI/SalI DNA fragment into the EcoRI/SalI site of pG210ShCT[G].

After pG210ShCT[G] was digested with restriction enzymes EcoRI and SalI, an about 3.5 kb DNA fragment containing the vector portion was prepared. This fragment was ligated with the about 280 bp DNA fragment of hProPTH (1-84) prepared in Example 1 to prepare pG210ShProPTH (FIG. 3). pG210ShProPTH was transformed into E. coli strain JM109 to prepare JM109 [pG210ShProPTH].

Further, linkers KM091 (SEQ ID NO: 15) and KM092 (SEQ ID NO: 16) were inserted into the restriction enzyme XhoI/EcoRI site of pG210ShProPTH to prepare plasmid pG210S (S/X) (FIG. 3). The above linker has restriction enzyme XhoI and EcoRI sites at respective both ends and SacI site therebetween.

pG210S (S/X) was digested with restriction enzymes SacI and XhoI, and a DNA region encoding βGal-210S was specifically deleted using Deletion Kit for Kilo-Sequence (manufactured by Takara Shuzo Co., Ltd.). Ends were repaired using a Klenow fragment, followed by self-ligation to prepare plasmid pGP#19 encoding a chimeric protein βGal-139S(FM)PPH84 with βGal-139S and hProPTH (1-84) bound thereto through Phe-Met (FIG. 4). E. coli strain JM109 with pGP#19 introduced thereinto was designated as "JM109[pGP#19]."

Example 3
Preparation of βGal-117SmHPPH34 Expression Plasmid pG117SmHPPH34

In this example, the preparation of βGal-117SmHPPH34 expression plasmid pG117SmHPPH34 will be described by way of example, and βGal-97SmHPPH34 expression plasmid pG97SmHPPH34 or βGal-139SmHPPH34 expression plasmid pG139SmHPPH34 can be prepared using βGal-97S or βGal-139S instead of βGal-117S.

Figure 5:
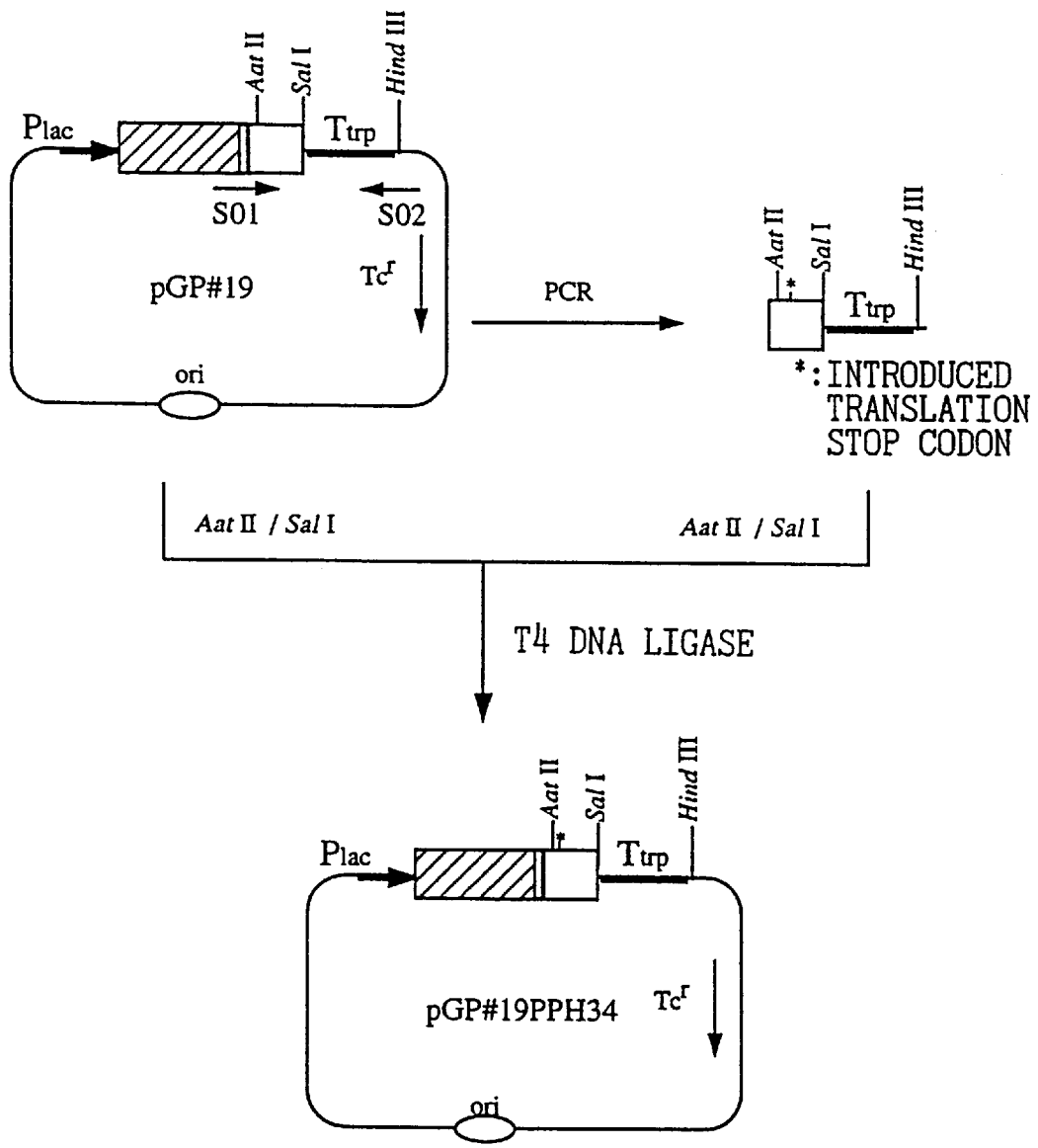
FIG. 5 is a diagram showing the preparation of a plasmid pGP#19PPH34 capable of expressing a chimeric protein βGal-139S(FM)PPH34.

1) Preparation of pGP#19PPH34 pGP#19PPH34 was prepared as follows. A DNA fragment of hPTH (1-84) with codon GTT of 35 Val being converted to translation stop codon TAA was amplified by PCR using pGP#19 as a template and S01 (SEQ ID NO: 17) and S02 (SEQ ID NO: 18) as primers. A restriction enzyme AatII-SalI DNA fragment was isolated and purified by a conventional method, followed by exchange with a portion corresponding to pGP#19 to prepare pGP#19PPH34 (FIG. 5).

2) Preparation of pG117SPPH34

Amplification was performed by PCR using pG210 (S/X) as a template and S03 (SEQ ID NO: 19) and S05 (SEQ ID NO: 20) as primers followed by digestion with restriction enzymes PvuI and SmaI to prepare a DNA fragment. Further, amplification was performed by PCR using pGP#19PPH34 as a template and S07 (SEQ ID NO: 21) and S02 as primers followed by digestion with restriction enzymes SalI and SmaI to prepare another DNA fragment. The above two DNA fragments and a restriction enzyme PvuI-SalI DNA fragment containing a replication origin for pGP#19PPH34 were ligated together using T4 ligase to prepare pG117SPPH34 (FIGS. 6 and 7).

3) Preparation of pG117SmHPPH34 (m=4 or 8)

pG117SmHPPH34 (m=4 or 8) was prepared by inserting linkers S08 (SEQ ID NO: 22) and S09 (SEQ ID NO: 23) encoding (His)$_4$-Pro-Gly and linkers S10 (SEQ ID NO: 24) and S11 (SEQ ID NO: 25) encoding {(His)$_4$-Pro-Gly}$_2$ into the restriction enzyme SmaI site of pG117SPPH34. In this connection, it should be noted that a plasmid (m=12, 16 or 24) can be prepared by varying the length of the linker (FIGS. 6 and 7).

Further, pG117S4KPPH34 was prepared by inserting linkers S12 (SEQ ID NO: 26) and S13 (SEQ ID NO: 27) encoding (Lys)$_4$-Pro-Gly into the restriction enzyme SmaI site of pG117SPPH34. Similarly, pG97S4kPPH34 and pG139S4kPPH34 can be prepared.

The number and direction of inserted linkers were confirmed by determining the DNA sequence after the preparation of plasmids, and chimeric proteins prepared in this example are tabulated in Table 1.

TABLE 1

|      | βGal-97SmHPPH34 | βGal-117SmHPPH34 | βGal-139SmHPPH34 |
|------|:---:|:---:|:---:|
| —    | ○ | ○ | ○ |
| 4H   | ○ | ○ |   |
| 8H   | ○ | ○ | ○ |
| 12H  | ○ | ○ | ○ |
| 16H  |   | ○ |   |
| 24H  |   | ○ |   |
| 4K   | ○ | ○ | ○ |

In the table, H represents a histidine residue, K represents a lysine residue, and the numeral attached to H or K represents the number of amino acids.

Example 4
Production of Chimeric Protein hPTH(1-34)

The productivity of the chimeric proteins listed in Table 1 were examined using SDS-PAGE.

16 plasmids containing a gene encoding a chimeric protein listed in Table 1 were each introduced into E. coli strain M25. Transformed cells were cultured in a test tube containing 2 ml of SB medium at 37° C. with shaking for 16 hours, followed by dilution with physiological saline to a culture turbidity (OD 660) of 10. An equal amount of an SDS sample buffer was added to 100 μl of the suspension, and the mixture was boiled for 3 min. 10 μl of the supernatant was subjected to SDS-PAGE to compare the amount of the chimeric protein produced per bacterium.

The results are shown in FIG. 8. As is apparent from FIG. 8, the amount of expressed chimeric protein varied depending upon the β-galactosidase derivative/number of histidine residues combination. Specifically, for βGal-97S, high productivity could be attained in the case of $\{(His)_4\text{-Pro-Gly}\}_n$ wherein n=2 and 3; for βGal-117S, high productivity could be attained in the case of $\{(His)_4\text{-Pro-Gly}\}_n$ wherein n=1, 2, 3, 4, and 6; and for βGal-139S, high productivity could be attained in the case of $\{(His)_4\text{-Pro-Gly}\}_n$ wherein n=2 and 3. In particular, for the derivatives of βGal-117S, the introduction of $\{(His)_4\text{-Pro-Gly}\}_n$, wherein n=1 to 6, resulted in markedly increased amount of expressed chimeric protein, and, in this case, the amount of the expressed chimeric protein was larger than that in the case of a mere change in charge by the lysine residue.

Example 5
Cleavage of hPTH(1-34) from Chimeric Protein

For the high productive chimeric proteins (βGal-97SmHPPH34 (m=12), βGal-117SmHPPH34 (m=0, 4, 8, 12, 16, and 24), and βGal-139SmHPPH34 (m=0 and 12 with m=0 being control), in order to investigate the suitability as a substrate for Kex2-660, the chimeric protein inclusion body was recovered, dissolved in 8M urea, and diluted to give a reaction composition (20 mM Tris/HCl (pH 8.2), 100 mM NaCl, 3.0M urea, 2.0 mM CaCl$_2$, 8 mg/ml chimeric protein). Kex2-660 was then added to a final concentration of 20 kU/ml to cleave hPTH (1-34). 90% or more of βGal-117SPPH34 as the control was excised under these conditions for one hr.

In FIG. 9, the reactivity of each derivative with Kex2-660 was expressed in terms of the ratio of kcat to pG117SPPH34. The quantitative determination of hPTH (1-34) was carried out according to the method described in the above "Basic experimental procedures." As a result, it was found that, for all the cases, the introduction of $\{(His)_4\text{-Pro-Gly}\}_n$, wherein n=1 to 6, further results in improved reactivity with Kex2-660.

In particular, for βGal-117S4HPPH34, it was found that the insertion of one $(His)_4$-Pro-Gly linker results improved production of the chimeric protein and reactivity with Kex2-660 and, in addition, offers a solubility of not less than 15 g/L under Kex2 reaction conditions, i.e., contributed to an improvement in solubility over the solubility of βGal-139SPPH34 (8 g/L).

Example 6
Mass Production of hPTH(1-34)

In order to mass-produce the chimeric protein βGal-117S4HPPH34, which had been found to be expressed with a high productivity and to be suitable as a substrate for Kex2-660, the plasmid pG117S4HPPH34 containing a gene encoding this chimeric protein was transformed into E. coli strain M25 (W3110/ompT) to prepare strain M25 [pG117S4HPPH34]. The strain M25[pG117S4HPPH34] was cultured using a medium (2% (w/v) yeast extract, 1% (w/v) trypton, 1.2% (w/v) K$_2$HPO$_4$, 0.3% (w/v) KH$_2$PO$_4$, and 0.5% (w/v) glycerol) contained in a 20 L culture tank at 37° C.

When the cell concentration reached OD660=1.0, IPTG (isopropyl β-thiogalactoside) was added to a final concentration of 1 mM, followed by further culture until the cell concentration reached OD660=12. The cells were harvested, suspended in TE (10 mM Tris/HCl, 1 mM EDTA (pH 8.0)). The suspension was subjected to a high pressure homogenization (Manton-Gaulin) to disrupt the cells. The homogenate was centrifuged to obtain precipitate containing chimeric protein, which was then washed with TE and deionized water. About 100 g of inclusion bodies containing chimeric protein were obtained from 20 L culture. To 250 ml of the suspension of the inclusion (160 g/L) were added 100 ml of 1M Tris/HCl (pH 8.2), 50 ml of 5M NaCl, 500 ml of deionized water, and 900 g of urea, and the mixture was stirred for 30 min in a thermostatic chamber kept for 30 min at 30° C. to dissolve the components, diluted with warmed deionized water, and brought to 5 L at 30° C.

50 ml of a 250 mM CaCl$_2$ solution was slowly added while stirring, and Kex2-660 was added thereto to 20 kU/ml. 2 hr after the addition of Kex2-660 (percentage cleavage: not less than 90%), pH was adjusted to 6.4 by the addition of acetic acid, followed by two-fold dilution with deionized water to coagulate and sediment the chimeric protein remaining unreacted and the protective peptide. Centrifugation was performed to obtain a supernatant containing hPTH (1-34). The supernatant was adjusted to pH 5.0 by the addition of acetic acid and passed through a cation exchange resin (SP Toyopearl) column equilibrated with a 10 mM sodium acetate buffer (pH 5.0) to adsorb hPTH (1-34), followed by elution of hPTH (1-34) with 0.4M NaCl.

Acetic acid was added to a final concentration of 3%, and the mixture was passed through a low-pressure reversed phase column (SokenODS-W) equilibrated with 3% (v/v) acetic acid to adsorb hPTH (1-34), followed by elution of hPTH (1-34) with a 30% (v/v) acetonitrile solution containing 3% (v/v) acetic acid. Acetonitrile was removed under reduced pressure, and the residue was filtered through a 0.22-μm membrane filter and purified on a reversed phase HPLC preparative column (TSKgelODS120T Φ 55×600). In this case, the elution was done using acetonitrile with a linear density gradient (A: 5% (v/v) acetic acid/10% (v/v) acetonitrile; B: 5% (v/v) acetic acid/40% (v/v) acetonitrile; %B=20%→80%/60 min) at a flow rate of 40 ml/min. The recovery of hPTH (1-34) for each step was tabulated in Table 2.

TABLE 2

Recovery of hPHT (1–34)

| Steps | Amount of PTH (g) | Recovery (%) |
|---|---|---|
| Reaction with Kex2-660 | 7.0 | 100 |
| Supernatant obtained upon precipitation with acid | 6.7 | 95 |
| Cation exchange column | 6.0 | 85 |
| Low-pressure reversed phase column | 5.8 | 82 |
| HPLC | 4.0 | 57 |

Example 7
Substitution of Amino Acids at Kex2-660 Recognition Site P3 of Chimeric Protein In order to convert amino acids at the P3 site (Lys) to different amino acids, oligonucleotides S14–S18 (SEQ ID NOS: 28 to 32) with a codon corresponding to the P3 site being converted were synthesized, and a DNA fragment was synthesized by PCR using these oligonucleotides and S02 (SEQ ID NO: 18) as primers and pG117S4HPPH34 as a template. The DNA fragment thus obtained was purified by ethanol precipitation, cleaved by StuI and SalI, and electrophoresed on 2.0% (w/v) agarose gel to purify a target 0.4 Kbp StuI-SalI fragment.

This DNA fragment was ligated with a DNA fragment, encoding a β galactosidase portion of pG117S4HPPH34, which had been prepared by digestion with StuI and SalI and conducting purification in the same manner as described just above in connection with the target StuI-SalI DNA fragment. After the completion of the ligation reaction, the ligation mixture was used to transform E. coli strain JM109. For each combinations, 10 tetracycline resistant clones were obtained, and plasmids from the clones were analyzed by DNA sequencing to obtain desired expression vectors.

That is, there was prepared an expression vector pG117S4HVXPH34 for a chimeric protein βGal-117S4HVXPH34 having an amino acid sequence wherein the Kex2-660 recognition site Ser-Val-Lys-Lys-Arg of a chimeric protein encoding pG117S4HPPH34 has been substituted with Ser-Val-X-Lys-Arg wherein X=Gly, Ala, Val, Leu, Ile, Ser, Thr, Asp, Glu, Asn, Gln, Lys, Arg, Phe, Tyr, Trp, His, or Pro SEQ ID NO: 58.

In order to investigate the reactivity of each chimeric protein with Kex2-660, each clone was cultured in 50 ml of an SB medium, and, when the cell concentration reached OD660=1.0, expression was induced by IPTG, followed by culture for additional 4 hr. Thereafter, cells were harvested, washed with a TE buffer, suspended, disrupted, and centrifuged to prepare inclusion bodies. Inclusion bodies were washed with 1% (w/v) Triton X100 containing 10 mM EDTA, and TE to prepare purified inclusion bodies. 90% or more of the peptide component contained in the inclusion body was a target chimeric protein. 20 μl of 1M Tris/HCl (pH 8.2), 20 μl of 5M NaCl, and 300 μl of 10M urea were added to and dissolved in a suspension of each chimeric protein inclusion body, the mixtures were then diluted with 650 μl of deionized water and held in a thermostatic chamber of 30° C. for 10 min, 10 μl of a 250 mM $CaCl_2$ solution was added thereto, and Kex2-660 was added to a concentration of 20 kU/ml.

Figure 10:
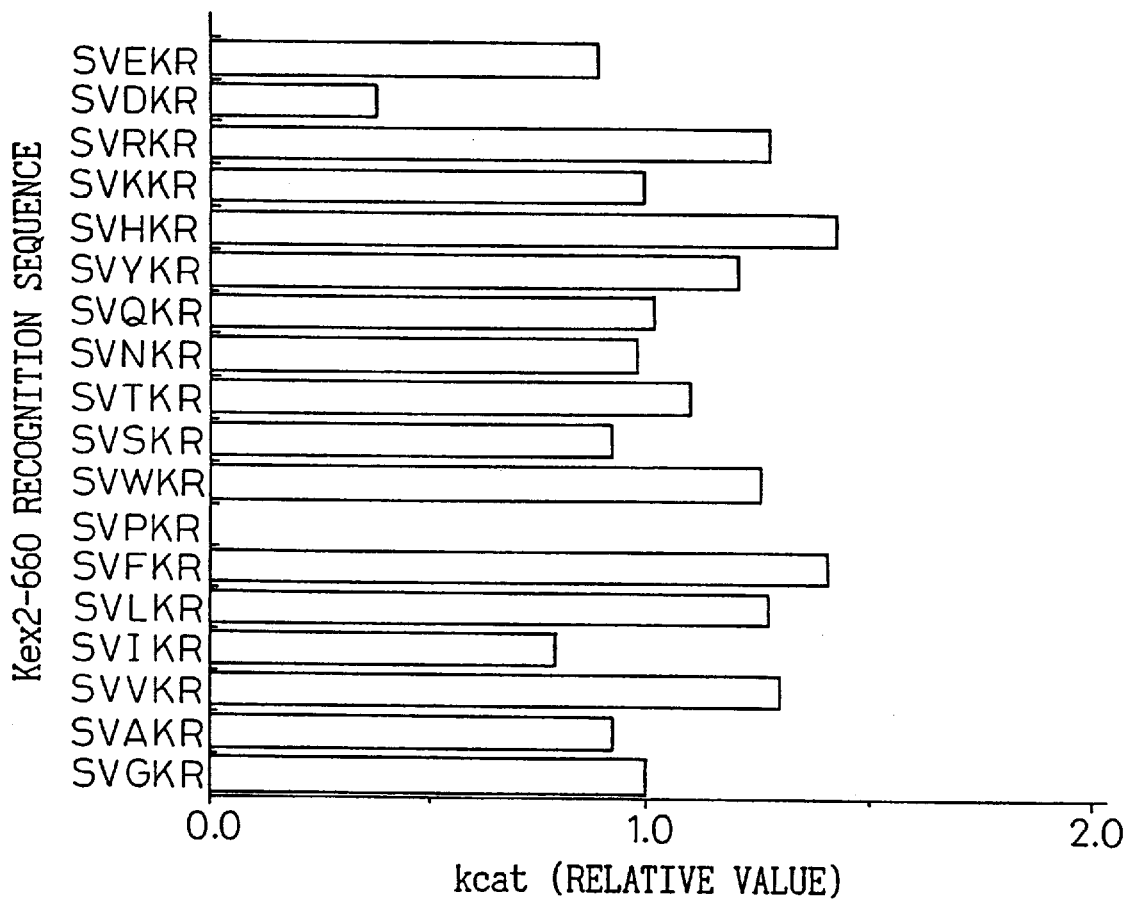
FIG. 10 is a diagram showing the influence of an amino acid at Kex2 protease recognition site P3 on the efficiency of the cleavage of hPTH (1-34) by Kex2-660, the amino acid at the site P4 being immobilized onto a valine residue with the amino acid at the site P3 being substituted, wherein the abscissa represents the relative kcat value with the kcat value of βGal-117S4HVKPH34 being supposed to be 1.

90% or more of βGal-117SPPH34 as the control was excised under these conditions for one hr. hPTH (1-34) produced was quantitatively determined by HPLC using the above ODS column. The reactivity of each derivative with Kex2-660 was expressed in terms of the ratio of kcat to pG117S4HPPH34 (FIG. 10). It was found that, when X=Phe or His, the cleavage efficiency of hPTH (1-34) by Kex2-660 is improved, whereas when X=Pro, substantially no hPTH (1-34) is excised by Kex2-660.

Example 8
Substitution of Amino Acids at Kex2-660 Recognition Site P4 of Chimeric Protein Based on the results of Example 7 and the fact that the amount of the by-product at the time of cleavage is small, a chimeric protein having a histidine residue at the P3 site, βGal-117S4HVHPH34, was selected as a chimeric protein for the production of hPTH (1-34), and an attempt has been made to substitute the amino acids at the P4 site to further improve the reactivity with Kex2-660. Oligonucleotides S19 to S24 (SEQ ID NOS: 33–38) were synthesized, and a DNA fragment with mutation being introduced thereinto was synthesized by PCR using the above oligonucleotides and S02 as primers and pG117S4HVHPPH34 as a template.

The procedure of Example 7 was repeated to prepare an expression vector pG117S4HXHPH34 for a chimeric protein βGal-117S4HXHPH34 having a structure wherein the Kex2-660 recognition site Ser-Val-His-Lys-Arg of the chimeric protein has been substituted with Ser-X-His-Lys-Arg wherein X=Gly, Ala, Leu, Ile, Ser, Thr, Asp, Glu, Asn, Gln, Lys, Arg, Cys, Met, Phe, Tyr, Trp, His, Pro, or Val SEQ ID NO: 54.

The sensitivity to Kex2-660 was judged using the chimeric proteins as the substrate under the same conditions as used in Example 6. As a result, it was found that when X=Lys or Arg, the efficiency of the cleavage of hPTH (1-34) by Kex2-660 is improved, whereas when X is an acidic amino acid (Asp or Glu), substantially no hPTH (1-34) is excised by Kex2-660 (FIG. 11). Thus, it has for the first time become apparent that Kex2-660 protease requires an arginine residue at the P1 site and a strongly basic amino acid or a proline residue at the P2 site and, at the same time, prefers a histidine residue or a phenylalanine residue at the P3 site and a strongly basic amino acid at the P4 site and that the presence of a proline residue at the P3 site or the presence of an acidic amino acid at the P4 site results in remarkably lowered chimeric protein cleaving activity.

Example 9
Removal of Kex2-660-Cleaved Site of Protective Peptide

The Kex2-660 cleaving reactions in Examples 7 and 8 were traced with the elapse of time by HPLC. As a result, it was found that a peptide bond on the C-terminal side of the sequence Arg-Arg at the 13- and 14 positions of the protective peptide βGal-117S was cleaved. Therefore, it was expected that the resultant βGal (1-14) is included at the time of purification of hPTH (1-34) by precipitation with an acid. Accordingly, an attempt has been made to substitute 14 Arg with Lys to inhibit cleaving by Kex2-660, thereby inhibiting the production of βGal (1-14).

Figure 12:
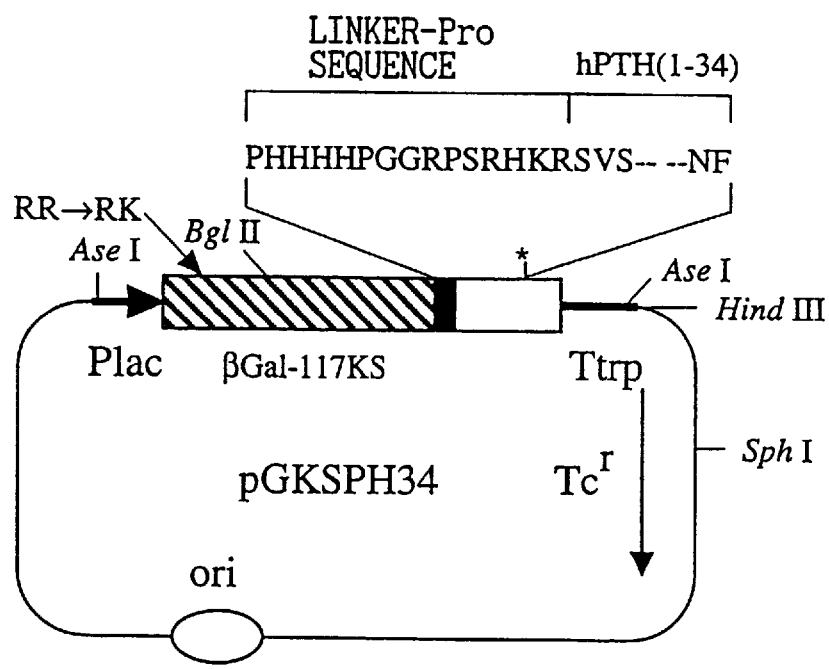
FIG. 12 is a typical diagram showing the structure of an expression vector pGKSPH34 for a βGal-117KS4HRHPH34 gene, wherein βGal-117KS is a peptide with an arginine residue at the 14-position of βGal-117S being substituted by a lysine residue.

A plasmid pGKSPH34 (FIG. 12) encoding a chimeric protein (βGal-117KS4HRHPH34) with 14 Arg being substituted with Lys was prepared as follows. At the outset, a DNA fragment with mutation being introduced thereinto, AseI-RK, was synthesized by PCR using an oligonucleotide S25 (SEQ ID NO: 39) and S26 (SEQ ID NO: 40) as primers and pG117S4HRHPH34 as a template. Similarly, a DNA fragment, RK-BglII, was prepared using an oligonucleotide S27 (SEQ ID NO: 41) and S28 (SEQ ID NO: 42) as primers.

Each DNA fragment was purified, and about 1 ng of each of the purified DNA fragments was weighed, the weighed fragments were mixed together, PCR was performed four times in the absence of primers to synthesize an AseI-BglII fragment with mutation being introduced thereinto. The oligonucleotides S25 and S28 were added, and PCR was further continued to amplify the fragment. The fragment was purified by ethanol precipitation, cleaved by AseI and BglII, electrophoresed on a 2.0% (w/v) agarose gel to prepare a target 0.35 kbp fragment. An AseI/SphI (1.8 kbp) fragment and a SphI/BglII (1.4 kbp) fragment of pG117S4HRHPH34 were electrophoresed on a 1.0% (w/v) agarose gel to purify these fragments.

The above three fragments were ligated together, and the ligation mixture was used to transform E. coli strain JM109. Tetracycline resistant clones were obtained, and plasmids prepared by alkali-lysis methods were analyzed by DNA sequencing. A target clone was selected which had a plasmid pGKSPH34 containing a gene wherein a DNA sequence CGG encoding 14 Arg of the protective peptide has been substituted with AAG. Inclusion bodies of chimeric proteins were obtained in the same manner as in Example 5. They were reacted with Kex2-660. As a result, it was found that the above substitution substantially completely inhibited cleaving of the protective peptide, lightening the burden imposed on the purification process.

Example 10
Mass-Production of Chimeric Protein βGal-117KS4HRHPH34 and Production of hPTH (1-34)

In the example, the production of the chimeric protein βGal-117KS4HRHPH34, under large scale culture conditions, which has been considered to be best suited as a substrate for Kex2-660 on a test tube level, the cleavage by Kex2-660 protease, and the purification of hPTH (1-34) were performed.

pGKSPH34 was used to transform E. coli strain M25 to tetracycline resistance to harvest tetracycline-resistant strains, followed by the preparation of a production strain M25[pGKSPH34]. The strain M25[pGKSPH34] was cultured on a large scale in an NU1 synthetic medium containing 2% (w/v) glucose.

After the consumption of glucose, glycerol was fed as a carbon source, and culture was performed for 24 hr while regulating pH to 7.0. The final cell concentration was 150 to 200 OD. This chimeric protein was stably produced under large scale culture conditions, and no significant inhibition of growth of the host E. coli despite the high level expression, was observed. The amount of the inclusion body produced was about 5 g/L. After disruption of the cells, insolubles were washed with TE and deionized water to prepare a purified inclusion body.

The inclusion body was solubilized with urea and diluted to give a reaction solution composition of 20 mm Tris/HCl (pH 8.2), 50 mM NaCl, 2.5 mM $CaCl_2$, 2.7M urea, and 8.0 mg/ml chimeric protein. At a reaction temperature of 30° C., Kex2-660 was added to a concentration of 5 kU/ml to cleavage hPTH (1-34) from the chimeric protein, and the production of hPTH (1-34) was quantitatively determined. As a result, 30 min after the initiation of the reaction, the percentage cleavage reached 90% or more, and the amount of Kex2-660 was decreased to ¼ as compared with βGal-117S4HPH34. After the completion of the reaction, hPTH (1-34) was purified in the same manner as in Example 5. The recovery in the purification process was substantially the same as that in Example 5.

Example 11
Preparation of βGal-117S4HGP Production Plasmid, pG117S4HGP

A plasmid which produces a chimeric protein (βGal-117S4HGP) containing a human glucagon-like peptide I (hGLP-1 (7-37)), pG117S4HGP, was constructed according to the following procedure. At the outset, four DNAs shown in FIG. 14 (a) (GLP-1 (SEQ ID NO: 43), GLP-2 (SEQ ID NO: 44), GLP-3 (SEQ ID NO: 45), and GLP-4 (SEQ ID NO: 46)) were synthesized. These DNAs at the 5'-terminal were phosphorylated with T4 polynucleotide kinase, mixed together, and annealed to prepare a hGLP-1 (7-37) gene (DNA(I)). On the other hand, two synthetic DNAs (117S4H SphI primer (SEQ ID NO: 47) and 117S4H BglII primer (SEQ ID NO: 48)) shown in FIG. 14 (b) were used as a primer for PCR, and PCR was performed using pGKSPH34 as a template. The resultant PCR product was digested with BglII and SphI to prepare a DNA fragment having BglII and SphI sticky ends (DNA (II)).

Then, pGKSPH34 was digested with BglII and SalI and electrophoresed on a 1% agarose gel to recover a larger DNA fragment (DNA(III)) from the gel. DNA(I), DNA(II), and DNA(III) thus obtained were ligated together using a T4 DNA ligase to prepare pG117S4HGP (FIG. 15).

Example 12
Production of Chimeric Protein βGal-117S4HGP

E. coli strain W3110M25 having the above-prepared pG117S4HGP was cultured in a medium containing 1.5% glucose, 4 g/l $K_2HPO_4$, 4 g/l $KH_2PO_4$, 2.7 g/l $Na_2HPO_4$, 0.2 g/l $NH_4Cl$, 1.2 g/l $(NH_4)_2SO_4$, 4 g/l yeast extract, 2 g/l L-methionine, 2 g/l $MgSO_4.7H_2O$, 40 mg/l $CaCl_2.2H_2O$, 40 mg/l $FeSO_4.7H_2O$, 10 mg/l $MnSO_4.nH_2O$, 10 mg/l $AlCl_3.H_2O$, 4 mg/l $CoCl_2.6H_2O$, 2 mg/l $ZnSO_4.7H_2O$, 2 mg/l $Na_2MoO_4.2H_2O$, 1 mg/l $CuCl_2.2H_2O$, 0.5 mg/l $H_3BO_4$, and 10 mg/l tetracycline under conditions of 32° C. and pH 7.0. After exhaustion of glucose, glycerin was used as the carbon source, and culture was continued at 37° C. for additional 8 hr to produce inclusion bodies of βGal-117S4HGP in the bacterium. After the completion of the culture, the culture was then homogenized by means of a Manton-Gaulline homogenizer (model 15M-8TA, manufactured by Manton-Gaulline) at 600 KG/cm$^2$ and centrifuged (CEPA centrifuge) to recover a precipitate fraction. The precipitate was suspended in a buffer (10 mM Tris-HCl (pH 8.0), 1 mM EDTA) in an amount equal to that of the culture, again recovered by centrifugation, and suspended in deionized water in an amount equal to that of the culture. Thereafter, centrifugation was again performed to recover the precipitate which was then suspended in deionized water in an amount equal to that of the precipitate and used in the subsequent procedure.

Example 13
Cleavage of hGLP-1(7-37) from Chimeric Protein

The chimeric protein inclusion body prepared in Example 12 was recovered, dissolved in 8M urea, and diluted to give a reaction composition (20 mM Tris/HCl (pH 8.2), 100 mM NaCl, 3.0M urea, 2.0 mM $CaCl_2$, 8 mg/ml chimeric protein). Kex2-660 was then added to a final concentration of 10,000 U/ml to cleavage hGLP-1 (7-37). 90% or more of βGal-117S4HGP as the control was cleaved under these conditions for one hr.

Example 14
Fractionation of hGLP-1 (7-37) (FIG. 16, Table 3)

In order to mass-produce the chimeric protein βGal-117S4HGP, which had been found to be expressed with a high productivity and to be suitable as a substrate for Kex2-660, the plasmid pG117S4HGP encoding this chimeric protein was transformed into E. coli strain M25 (W3110/ompT), followed by culture in a 20 L culture tank. The medium comprised 20 g/L yeast extract, 10 g/L bactotriptone, 12 g/L $K_2HPO_4$, 3 g/L $KH_2PO_4$, and 5 g/L glycerin. When the cell concentration reached OD660=1.0, IPTG (isopropyl β-thiogalactoside) was added to a final concentration of 1 mM. An antifoaming agent (DISFOAM CC-222, manufactured by Nippon Oils & Fats Co., Ltd.) was used. The culture was continued at 37° C. until the cell concentration reached OD660=12. The cells were harvested and suspended in TE (10 mM Tris/HCl, 1 mM EDTA (pH 8.0)). The suspension was subjected to a high pressure homogenization (Manton-Gaulin) to disrupt the cells. The homogenate was centrifuged to obtain precipitate containing chimeric protein, which was then washed with TE and deionized water. About 100 g of inclusion bodies containing chimeric protein were obtained from 20 L culture. To 250 ml of the suspension of the inclusion (160 g/L) were added 100 ml of 1M Tris/HCl (pH 8.2), 50 ml of 5M NaCl, 500 ml of deionized water, and 900 g of urea, and the mixture was stirred for 30 min in a thermostatic chamber kept at 30° C. to dissolve the components, diluted with warmed deionized water, and brought to 5 L at 30° C. 50 ml of a 250 mM $CaCl_2$ solution was slowly added while stirring, and Kex2-660 was added thereto to 20,000 U/ml (about 4.0 mg/L). 2 hr after the addition of Kex2-660 (percentage cleavage: not less than 90%), pH was adjusted to 6.4 by the addition of acetic acid, followed by two-fold dilution with deionized water to coagulate and sediment the chimeric protein remaining unreacted and the protective peptide. Centrifugation was performed to obtain a supernatant containing hGLP-1 (7-37). The supernatant was adjusted to pH 5.0 by the addition of acetic acid and passed through a cation exchange resin (SP Toyopearl) column equilibrated with a 2M urea/10 mM sodium acetate buffer (pH 5.0) to adsorb hGLP-1 (7-37), followed by washing with a 2M urea/10 mM sodium acetate buffer (pH 6.2) and elution of hGLP-1 (7-37) with a sodium chloride density gradient from 0M to 300 mM. Acetic acid was previously placed in the fraction tube so as to give a final concentration of 3%, preventing the coagulation of hGLP-1 (7-37). A fraction containing hGLP-1 (7-37) was collected and passed through a low-pressure reversed phase column (Soken ODS-W) equilibrated with 5% acetic acid to adsorb hGLP-1 (7-37), followed by elution of hGLP-1 (7-37) with a 50% acetonitrile solution containing 5% acetic acid. Acetonitrile was removed under reduced pressure, and the residue was filtered through a 0.22-μm membrane filter and lyophilized.

The quantitative determination of hGLP-1 (7-37) will be described in detail. A solution containing hGLP-1 (7-37) subjected to 10- to 20-fold dilution with a sample buffer (1M acetate/2M urea), and the diluted solution is centrifuged to obtain a supernatant. The supernatant is then applied to HPLC (LC10A, manufactured by Shimadzu Seisakusho Ltd.) to which YMC-C8-A302 (4.6 mm I.D.×150 mm) column (manufactured by K.K. Yamamura Kagaku Kenkyujo) has been connected, followed by development of 10 to 20 μl of the supernatant using liquid A (0.1% TFA/10% acetonitrile) and liquid B (0.094% TFA/60% acetonitrile) with gradient B 40%→80%/20 min. The amount of hGLP-1 (7-37) is determined from the ratio of the peak area for hGLP-1 (7-37) to the peak area for standard hGLP-1 (7-37) having a known concentration, the peaks being detected by determination of absorbance at 220 nm. The recovery is given in Table 3.

TABLE 3

| Recovery of hGLP-1 (7–37) | | | |
|---|---|---|---|
| Steps | Volume/[l] | hGLP-1/[g] | Recovery/[%] |
| Kex2-660 reaction | 4.0 | 4.8 | 100 |
| Supernatant obtained upon precipitation with acid | 7.8 | 3.3 | 68 |
| Cation exchange column | 0.5 | 2.8 | 60 |
| Low-pressure reversed phase column | | 2.0 | 40 |

SEQUENCE LISTING

< 1 6 0 > 54

< 2 1 0 > 1
< 2 1 1 > 40
< 2 1 2 > DNA
< 2 1 3 > Artificial Sequence

< 2 2 0 >
< 2 2 3 > Description of Artificial Sequence:fragment U1 of hProPTH

< 4 0 0 > 1 aattcatgaa atctgttaaa aagcgttctg tttctgaaat          40

< 2 1 0 > 2
< 2 1 1 > 41
< 2 1 2 > DNA
< 2 1 3 > Artificial Sequence

< 2 2 0 >
< 2 2 3 > Description of Artificial Sequence:fragment U2 of hProPTH

<400> 2
tcagctgatg cataacctgg gcaaacacct gaatagcatg g    41

<210> 3
<211> 41
<212> DNA
<213> Artificial Sequence

<220>
<223> Description of Artificial Sequence:fragment U3 of
      hProPTH

<400> 3
aacgcgtcga gtggctgcgt aagaaactgc aggacgtcca c    41

<210> 4
<211> 41
<212> DNA
<213> Artificial Sequence

<220>
<223> Description of Artificial Sequence:fragment U4 of
      hProPTH

<400> 4
aacttcgttg cgctgggtgc accgctggct ccacgtgatg c    41

<210> 5
<211> 39
<212> DNA
<213> Artificial Sequence

<220>
<223> Description of Artificial Sequence:fragment U5 of
      hProPTH

<400> 5
aggatcccaa cgtccgcgta agaaagaaga taacgtact    39

<210> 6
<211> 40
<212> DNA
<213> Artificial Sequence

<220>
<223> Description of Artificial Sequence:fragment U6 of
      hProPTH

<400> 6
ggttgaatct catgagaaat ccctgggcga agctgacaaa    40

<210> 7
<211> 40
<212> DNA
<213> Artificial Sequence

<220>
<223> Description of Artificial Sequence:fragment U7 of
      hProPTH

<400> 7
gccgatgtta acgtgctgac caaagcgaaa agccagtaag    40

<210> 8
<211> 33
<212> DNA
<213> Artificial Sequence

```
<210> 8 (continuation)
<220>
<223> Description of Artificial Sequence:fragment L1 of
      hProPTH

<400> 8
tcgacttact ggcttttcgc tttggtcagc acg                          33

<210> 9
<211> 40
<212> DNA
<213> Artificial Sequence

<220>
<223> Description of Artificial Sequence:fragment L2 of
      hProPTH

<400> 9
ttaacatcgg ctttgtcagc ttcgcccagg gatttctcat                   40

<210> 10
<211> 40
<212> DNA
<213> Artificial Sequence

<220>
<223> Description of Artificial Sequence:fragment L3 of
      hProPTH

<400> 10
gagattcaac cagtacgtta tcttctttct tacgcggacg                   40

<210> 11
<211> 41
<212> DNA
<213> Artificial Sequence

<220>
<223> Description of Artificial Sequence:fragment L4 of
      hProPTH

<400> 11
ttgggatcct gcatcacgtg gagccagcgg tgcacccagc g                 41

<210> 12
<211> 41
<212> DNA
<213> Artificial Sequence

<220>
<223> Description of Artificial Sequence:fragment L5 of
      hProPTH

<400> 12
caacgaagtt gtggacgtcc tgcagtttct tacgcagcca c                 41

<210> 13
<211> 40
<212> DNA
<213> Artificial Sequence

<220>
<223> Description of Artificial Sequence:fragment L6 of
      hProPTH

<400> 13
tcgacgcgtt ccatgctatt caggtgtttg ccaggttatg                   40

<210> 14
```

<211> 46
<212> DNA
<213> Artificial Sequence

<220>
<223> Description of Artificial Sequence:fragment L7 of hProPTH

<400> 14
catcagctga atttcagaaa cagaacgctt tttaacagat ttcatg　46

<210> 15
<211> 24
<212> DNA
<213> Artificial Sequence

<220>
<223> Description of Artificial Sequence:linker KM091

<400> 15
tcgaggtcga cggtaccgag ctcg　24

<210> 16
<211> 24
<212> DNA
<213> Artificial Sequence

<220>
<223> Description of Artificial Sequence:linker KM092

<400> 16
aattcgagct cggtaccgtc gacc　24

<210> 17
<211> 45
<212> DNA
<213> Artificial Sequence

<220>
<223> Description of Artificial Sequence:primer S01

<400> 17
aaactgcagg acgtccacaa cttctaagcg ctgggtgcac cgcgt　45

<210> 18
<211> 24
<212> DNA
<213> Artificial Sequence

<220>
<223> Description of Artificial Sequence:primer S02

<400> 18
cattaaagct tgcgatgat aagc　24

<210> 19
<211> 26
<212> DNA
<213> Artificial Sequence

<220>
<223> Description of Artificial Sequence:primer S03

<400> 19
cgcaccgatc gcccttccca acagtt　26

<210> 20
<211> 35

-continued

<210> DNA
<213> Artificial Sequence

<220>
<223> Description of Artificial Sequence:primer S05

<400> 20
tttcccgggc ctccgtggga acaaacggcg gattg       35

<210> 21
<211> 42
<212> DNA
<213> Artificial Sequence

<220>
<223> Description of Artificial Sequence:primer S07

<400> 21
tttcccggga ggccttctgt taaaagcgg tctgtttctg aa       42

<210> 22
<211> 18
<212> DNA
<213> Artificial Sequence

<220>
<223> Description of Artificial Sequence:primer S08

<400> 22
caccatcatc accctgga       18

<210> 23
<211> 18
<212> DNA
<213> Artificial Sequence

<220>
<223> Description of Artificial Sequence:primer S09

<400> 23
tccagggtga tgatggtg       18

<210> 24
<211> 36
<212> DNA
<213> Artificial Sequence

<220>
<223> Description of Artificial Sequence:primer S010

<400> 24
caccaccatc atcctggaca ccatcatcac cctgga       36

<210> 25
<211> 36
<212> DNA
<213> Artificial Sequence

<220>
<223> Description of Artificial Sequence:primer S11

<400> 25
tccagggtga tgatggtgtc caggatgatg gtggtg       36

<210> 26
<211> 18
<212> DNA
<213> Artificial Sequence

<220>
<223> Description of Artificial Sequence:primer S12

<400> 26
aagaagaaga agcctgga 18

<210> 27
<211> 18
<212> DNA
<213> Artificial Sequence

<220>
<223> Description of Artificial Sequence:primer S13

<400> 27
tccggacttc ttcttctt 18

<210> 28
<211> 36
<212> DNA
<213> Artificial Sequence

<220>
<223> Description of Artificial Sequence:primer S14

<220>
<221> misc_feature
<222> (16)..(36)
<223> The undefined nucleotide at position 16 is any
        nucleotide which results in a codon that encodes
        an amino acid.

<400> 28
gggaggcctt ctgttncaaa gctttctgtt tctgaa 36

<210> 29
<211> 36
<212> DNA
<213> Artificial Sequence

<220>
<223> Description of Artificial Sequence:primer S15

<220>
<221> misc_feature
<222> (16)..(36)
<223> The undefined nucleotide at position 16 is any
        nucleotide which results in a codon that encodes
        an amino acid.

<400> 29
gggaggcctt ctgttnataa gctttctgtt tctgaa 36

<210> 30
<211> 36
<212> DNA
<213> Artificial Sequence

<220>
<223> Description of Artificial Sequence:primer S16

<220>
<221> misc_feature
<222> (16)..(36)
<223> The undefined nucleotide at position 16 is any
        nucleotide which results in a codon that encodes
        an amino acid.

<400> 30
gggaggcctt ctgttnttaa gctttctgtt tctgaa 36

<210> 31
<211> 36
<212> DNA
<213> Artificial Sequence

<220>
<223> Description of Artificial Sequence:primer S17

<220>
<221> misc_feature
<222> (16)..(36)
<223> The undefined nucleotide at position 16 is any
      nucleotide which results in a codon that encodes
      an amino acid.

<400> 31
gggaggcctt ctgttbggaa gctttctgtt tctgaa                    36

<210> 32
<211> 36
<212> DNA
<213> Artificial Sequence

<220>
<223> Description of Artificial Sequence:primer S18

<220>
<221> misc_feature
<222> (16)..(36)
<223> The undefined nucleotide at position 16 is any
      nucleotide which results in a codon that encodes
      an amino acid.

<400> 32
gggaggcctt ctgttsaaaa gctttctgtt tctgaa                    36

<210> 33
<211> 33
<212> DNA
<213> Artificial Sequence

<220>
<223> Description of Artificial Sequence:primer S19

<220>
<221> misc_feature
<222> (14)..(33)
<223> The undefined nucleotide at position 14 is any
      nucleotide which results in a codon that encodes
      an amino acid.

<400> 33
gggaggcctt ctadtcataa gctttctgtt tct                       33

<210> 34
<211> 33
<212> DNA
<213> Artificial Sequence

<220>
<223> Description of Artificial Sequence:primer S20

<220>
<221> misc_feature
<222> (14)..(33)
<223> The undefined nucleotide at position 14 is any
      nucleotide which results in a codon that encodes
      an amino acid.

<400> 34
gggaggcctt ctahgcataa gctttctgtt tct                       33

<210> 35
<211> 33
<212> DNA
<213> Artificial Sequence

<220>
<223> Description of Artificial Sequence:primer S21

<220>
<221> misc_feature
<222> (14)..(33)
<223> The undefined nucleotide at position 14 is any
      nucleotide which results in a codon that encodes
      an amino acid.

<400> 35
gggaggcctt ctghgcataa gctttctgtt tct       33

<210> 36
<211> 33
<212> DNA
<213> Artificial Sequence

<220>
<223> Description of Artificial Sequence:primer S22

<220>
<221> misc_feature
<222> (14)..(15)
<223> The undefined nucleotides at positions 14 and 15
      are any nucleotides which result in a codon that
      encodes an amino acid.

<400> 36
gggaggcctt cttkkcataa gctttctgtt tct       33

<210> 37
<211> 34
<212> DNA
<213> Artificial Sequence

<220>
<223> Description of Artificial Sequence:primer S23

<220>
<221> misc_feature
<222> (14)..(34)
<223> The undefined nucleotide at position 14 is any
      nucleotide which results in a codon that encodes
      an amino acid.

<400> 37
gggaggcctt ctcvacataa gctttctgtt tctg      34

<210> 38
<211> 34
<212> DNA
<213> Artificial Sequence

<220>
<223> Description of Artificial Sequence:primer S24

<220>
<221> misc_feature
<222> (13)..(34)
<223> The undefined nucleotide at position 13 is any
      nucleotide which results in a codon that encodes
      an amino acid.

<400> 38
gggaggcctt ctbatcataa gctttctgtt tctg      34

<210> 39
<211> 27
<212> DNA
<213> Artificial Sequence

<220>
<223> Description of Artificial Sequence:primer S25

<400> 39
aattaatgtg agttagctca ccattag     27

<210> 40
<211> 24
<212> DNA
<213> Artificial Sequence

<220>
<223> Description of Artificial Sequence:primer S26

<400> 40
atcccagtct ttagcttgta aaac     24

<210> 41
<211> 24
<212> DNA
<213> Artificial Sequence

<220>
<223> Description of Artificial Sequence:primer S27

<400> 41
gttttacaac gtaaagactg ggat     24

<210> 42
<211> 31
<212> DNA
<213> Artificial Sequence

<220>
<223> Description of Artificial Sequence:primer S28

<400> 42
tttagatctg actccagcaa gctgtccggc a     31

<210> 43
<211> 57
<212> DNA
<213> Artificial Sequence

<220>
<223> Description of Artificial Sequence:oligonucleotide
      GLP-1

<400> 43
cggaaggtac ctttaccagc gatgtgagct cgtatctgga aggtcaggcg gcaaaag     57

<210> 44
<211> 48
<212> DNA
<213> Artificial Sequence

<220>
<223> Description of Artificial Sequence:oligonucleotide
      GLP-2

<400> 44
accttccaga tacgagctca catcgctggt aaaggtacct tccgcatg     48

<210> 45
<211> 36
<212> DNA
<213> Artificial Sequence

<220>
<223> Description of Artificial Sequence:oligonucleotide
GLP-3

<400> 45
aattcatcgc gtggctggtg aaaggccgtg gttaag         36

<210> 46
<211> 53
<212> DNA
<213> Artificial Sequence

<220>
<223> Description of Artificial Sequence:oligonucleotide
GLP-4

<400> 46
tcgacttaac cacggccttt caccagccac gcgatgaatt cttttgccgc ctg         53

<210> 47
<211> 38
<212> DNA
<213> Artificial Sequence

<220>
<223> Description of Artificial Sequence:117S4H SphI
primer

<400> 47
tgaatttcag aagcatgccg cttatgtcga gaaggcct         38

<210> 48
<211> 24
<212> DNA
<213> Artificial Sequence

<220>
<223> Description of Artificial Sequence:117S4H BglII
primer

<400> 48
gactcagatc ttcctgaggc cgat         24

<210> 49
<211> 6
<212> PRT
<213> Artificial Sequence

<220>
<223> Description of Artificial Sequence:exemplary
linker peptide

<400> 49

His His His His Pro Gly
 1               5

<210> 50
<211> 4
<212> PRT
<213> Artificial Sequence

<220>
<223> Description of Artificial Sequence:linker peptide;

x1 is any amino acid except asp and glu; x2 is any
amino acid except pro; x3 is lys, arg or pro

<400> 50

Xaa Xaa Xaa Arg
 1

<210> 51
<211> 8
<212> PRT
<213> Artificial Sequence

<220>
<223> Description of Artificial Sequence:linker peptide

<400> 51

Tyr Met Leu Ser Val Leu Leu Arg
 1               5

<210> 52
<211> 15
<212> PRT
<213> Artificial Sequence

<220>
<223> Description of Artificial Sequence:modified
      Kex2-660 recognition site; x is gly, ala, val,
      leu, ile, ser, thr, asp, glu, asn, gln, lys, arg,
      phe, tyr, trp, his, or pro

<400> 52

Pro His His His His Pro Gly Gly Arg Pro Ser Arg His Leu Arg
 1               5                  10                  15

<210> 53
<211> 5
<212> PRT
<213> Artificial Sequence

<220>
<223> Description of Artificial Sequence:Kex2-660
      recognition sequence; xaa is gly, ala, val, leu,
      ile, ser, thr, asp, glu, asn, gln, lys, arg, phe,
      tyr, trp, his, or pro

<400> 53

Ser Val Xaa Leu Arg
 1               5

<210> 54
<211> 5
<212> PRT
<213> Artificial Sequence

<220>
<223> Description of Artificial Sequence:modified
      Kex2-660 regonition sequence; xaa is gly ala leu
      ile ser thr asp glu asn gln lys arg cys met phe
      tyr trp his pro or val

<400> 54

Ser Xaa His Leu Arg
 1               5

We claim:

1. A chimeric protein of the formula:

A-L-B wherein A is a protective peptide; B is a target peptide; and L is a linker peptide having the sequence $X_1$-$X_2$-(Pro, Lys, or Arg)-Arg in its C-terminal region and a domain rich in his in its N-terminal region, wherein $X_1$ is any amino acid except Asp and Glu, and $X_2$ is any amino acid except Pro.

2. The chimeric protein according to claim 1, wherein the domain rich in His in the N-terminal region has the sequence: [(His)$_4$-Pro-Gly SEQ ID NO: 49]$_n$ wherein n is 1 to 6.

3. The chimeric protein according to claim 1, wherein any 1 to 5 amino acids exist between the amino acid sequence in the N-terminal region and the amino acid sequence in the C-terminal region.

4. The chimeric protein according to claim 1, wherein, in the C-terminal region, $X_1$ is Arg, Lys or His and $X_2$ is His or Phe.

5. The chimeric protein according to claim 1, wherein A represents a polypeptide not containing the amino acid sequence: Pro-Arg, Arg-Arg, and Lys-Arg.

6. The chimeric protein according to claim 1, wherein when A represents a polypeptide containing the amino acid sequence: Pro-Arg, Arg-Arg, or Lys-Arg, at least one amino acid in said amino acid sequence has been substituted with a different amino acid so as for A not to contain said amino acid sequence.

7. The chimeric protein according to claim 1, wherein A represents a polypeptide of not more than 220 amino acid residues.

8. The chimeric protein according to claim 7, wherein A represents a peptide of amino acids 1-97, 1-117, or 1-139 on the N-terminal side of β-galactosidase derived from *E. coli*.

9. The chimeric protein according to claim 1, wherein any cysteine in A has been substituted with a different amino acid.

10. The chimeric protein according to claim 9, wherein the different amino acid is serine.

11. The chimeric protein according to claim 1, wherein B represents a human parathyroid hormone or a derivative having the biological activity of human parathyroid hormone.

12. The chimeric protein according to claim 11, wherein the human parathyroid hormone derivative comprises a fragment comprising amino acids from 1 or 3 to 31, 34, 37, 38, or 84 in the N-terminal of a naturally occurring human parathyroid hormone, or a fragment comprising said amino acid residues with Gly being further added to the C-terminal.

13. The chimeric protein according to claim 1, wherein B represents glucagon-like-peptide 1 or a derivative having the biological activity of glucagon-like-peptide 1.

14. A process for producing the chimeric protein according to claim 1, comprising the steps of: transforming an expression vector containing DNA encoding the chimeric protein into a host cell; culturing the resultant transformants; and harvesting the chimeric protein from the culture.

15. A process for producing a target peptide (B), wherein a processing enzyme acts on the chimeric protein according to claim 1 and cleaves a peptide bond between the C-terminal of the linker peptide (L) and the N-terminal of the target peptide (B) to produce the target peptide (B).

16. The process according to claim 15, wherein the processing enzyme is a member selected from Kex2 protease, furin, a prohormone convertase 1/3 (PC1/3), a prohormone convertase 2 (PC2), and derivatives having the enzymatic activity of such processing enzymes.

17. The process according to claim 15, wherein the target peptide (B) is recovered by isoelectric precipitation.

* * * * *